United States Patent
Panousis

(10) Patent No.: US 8,569,461 B2
(45) Date of Patent: Oct. 29, 2013

(54) HUMANIZED ANTI-INTERLEUKIN 3 RECEPTOR ALPHA CHAIN ANTIBODIES

(75) Inventor: Con Panousis, Bundoora (AU)

(73) Assignee: CSL Limited, Parkville (AU)

( * ) Notice: Subject to any disclaimer, the term of this patent is extended or adjusted under 35 U.S.C. 154(b) by 0 days.

(21) Appl. No.: 13/256,926

(22) PCT Filed: Aug. 17, 2011

(86) PCT No.: PCT/AU2011/001056
§ 371 (c)(1),
(2), (4) Date: Apr. 23, 2012

(87) PCT Pub. No.: WO2012/021934
PCT Pub. Date: Feb. 23, 2012

(65) Prior Publication Data
US 2013/0137855 A1    May 30, 2013

Related U.S. Application Data

(60) Provisional application No. 61/374,489, filed on Aug. 17, 2010.

(30) Foreign Application Priority Data

Feb. 17, 2011    (AU) .................. PCT/AU2011/000155

(51) Int. Cl.
*C07K 16/00*    (2006.01)
*C07K 16/28*    (2006.01)
(52) U.S. Cl.
USPC .................................. 530/387.3; 530/388.22

(58) Field of Classification Search
None
See application file for complete search history.

(56) References Cited

U.S. PATENT DOCUMENTS

| 2007/0135620 A1 | 6/2007 | Chamberlain et al. |
| 2008/0260731 A1 | 10/2008 | Bernett et al. |
| 2013/0084282 A1* | 4/2013 | Vairo et al. ................. 424/133.1 |

FOREIGN PATENT DOCUMENTS

| WO | WO-2009-070844 A1 | 6/2009 |
| WO | WO-2010-126066 | 4/2010 |
| WO | WO-2010-094068 | 8/2010 |

OTHER PUBLICATIONS

International Search Report on Patentability for International Application No. PCT/AU2011/001056, dated Aug. 17, 2011.
International Search Report and Written Opinion for International Application No. PCT/AU2011/001056, mailed Nov. 1, 2011.
Sun, Q., et al., "Monoclonal antibody 7G3 recognizes the N-terminal domain of the human interleukin-3 (Il-3) receptor alpha-chain and functions as a specific IL3 receptor antagonist", Blood, 87: 83-92. 1996.
Examination Report for United Kingdom application GB1211289.2, dated Oct. 31, 2012.

* cited by examiner

*Primary Examiner* — Elizabeth C Kemmerer
*Assistant Examiner* — Regina M Deberry
(74) *Attorney, Agent, or Firm* — Cooley LLP

(57) ABSTRACT

The present disclosure provides antibodies that bind to interleukin-3 receptor alpha chain and uses thereof.

4 Claims, 5 Drawing Sheets

HUMANIZED ANTI-INTERLEUKIN 3 RECEPTOR ALPHA CHAIN ANTIBODIES

RELATED APPLICATION DATA

The present application is a national phase application under 35 USC 371 of International Application No. PCT/AU2011/001056 filed on 17 Aug. 2011 which claims priority from U.S. Patent Application No. 61/374,489 entitled "Humanized Anti-Interleukin 3 Receptor Alpha Chain Antibodies" filed on 17 Aug. 2010 and from International Patent Application No: PCT/AU2011/000155 filed on 17 Feb. 2011 entitled "Compositions and Methods for Targeting Type 1 Interferon Producing Cells". The entire contents of these applications are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CSLL_001_01US_ST25.txt. The text file is about 28 KB, was created on Apr. 23, 2012, and is being submitted electronically via EFS-Web.

FIELD

The present disclosure relates to anti-interleukin 3 receptor alpha chain antibodies and uses thereof.

BACKGROUND

The functional interleukin 3 receptor is a heterodimer that comprises a specific alpha chain (IL-3Rα; CD123) and a "common" IL-3 receptor beta chain ($\beta_c$; CD131) that is shared with the receptors for granulocyte macrophage colony stimulating factor (GM-CSF) and interleukin 5 (IL-5).

IL-3Rα is a type I transmembrane protein with a deduced Molecular Weight of about 41 kDa containing an extracellular domain involved in IL-3 binding, a transmembrane domain and a short cytoplasmic tail of about 50 amino acids. The extracellular domain is composed of two regions: an N-terminal region of about 100 amino acids, the sequence of which exhibits similarity to equivalent regions of the GM-CSF and IL-5 receptor alpha-chains; and a region proximal to the transmembrane domain that contains four conserved cysteine residues and a WSXWS motif, common to other members of this cytokine receptor family.

The IL-3 binding domain comprises about 200 amino acid residue cytokine receptor motifs (CRMs) made up of two Ig-like folding domains. The extracellular domain of IL-3Rα is highly glycosylated, with N-glycosylation necessary for both ligand binding and receptor signaling.

IL-3Rα is expressed widely throughout the hematopoietic system including hematopoietic progenitors, mast cells, erythroid cells, megakaryocytes, basophils, eosinophils, monocytes/macrophages, neutrophils and CD5+ B-lymphocytes. Non-hematopoietic cells such as plasmacytoid dendritic cells (pDCs), Leydig cells, endothelial cells and stromal cells also express IL-3Rα.

IL-3Rα is also expressed by cells involved in certain disease states including myelodysplastic syndrome, myeloid leukemia (for example, acute myelogenous leukemia (AML)), malignant lymphoproliferative disorders such as lymphoma, allergies and autoimmune disease, such as lupus, Sjögren's syndrome or scleroderma. Accordingly, anti-IL-3Rα antibodies are desirable for therapeutic applications.

SUMMARY

The present disclosure is based on the inventor's production of a humanized antibody that binds specifically to IL-3Rα. Following humanization, the inventor found that the affinity of the antibody for IL-3Rα was reduced. Accordingly, the inventor performed affinity maturation to improve the affinity of the antibody for IL-3Rα. Unpredictably, the affinity matured antibody included mutations in the framework regions (FRs) of the heavy chain variable region ($V_H$) and light chain variable region ($V_L$), as well as in CDR1 of the light chain.

The inventor also produced forms of this antibody capable of inducing enhanced levels of effector function.

The inventor also found that a particular modification to induce enhanced effector function resulted in an additional desirable property in that following administration of the modified antibody to a mammal the number of NK cells in the mammal were initially reduced, however then expanded to levels greater than prior to administration. The inventor has also shown that there is a correlation between the number of NK cells and lysis of target cells, e.g., leukemia cells.

The present disclosure is broadly directed to an immunoglobulin based on a murine antibody capable of specifically binding to an IL-3Rα chain.

In one example, the present disclosure provides an isolated or recombinant immunoglobulin that specifically binds to an IL-3Rα chain and comprises complementarity determining regions (CDRs) of a $V_L$ comprising a sequence set forth in SEQ ID NO: 8 and CDRs of a $V_H$ set forth in SEQ ID NO: 9.

The present disclosure additionally or alternatively provides an isolated or recombinant antibody or antigen binding fragment thereof, the antibody or antigen binding fragment capable of specifically binding to IL-3Rα chain and comprising CDRs of a $V_L$ comprising a sequence set forth in SEQ ID NO: 8 and CDRs of a $V_H$ set forth in SEQ ID NO: 9.

The present disclosure additionally or alternatively provides an isolated or recombinant humanized antibody or antigen binding fragment thereof, the antibody or antigen binding fragment capable of specifically binding to IL-3Rα chain and comprising CDRs of a $V_L$ comprising a sequence set forth in SEQ ID NO: 8 and CDRs of a $V_H$ set forth in SEQ ID NO: 9.

In one example, the present disclosure provides an isolated or recombinant immunoglobulin that specifically binds to an IL-3Rα chain and comprises amino acid sequences according to SEQ ID NOs: 2-7, respectively.

The present disclosure additionally or alternatively provides an isolated or recombinant antibody or antigen binding fragment thereof, the antibody or antigen binding fragment capable of specifically binding to IL-3Rα chain and comprising amino acid sequences according to SEQ ID NOs: 2-7.

The present disclosure additionally or alternatively provides an isolated or recombinant humanized antibody or antigen binding fragment thereof, the antibody or antigen binding fragment capable of specifically binding to IL-3Rα chain and comprising amino acid sequences according to SEQ ID NOs: 2-7.

For example, the immunoglobulin or antibody comprises: (i) a light chain variable region ($V_L$) comprising CDRs 1, 2 and 3 as set forth in SEQ ID NOs: 2, 3 and 4, respectively; and (ii) a heavy chain variable region ($V_H$) comprising CDRs 1, 2 and 3 as set forth in SEQ ID NOs: 5, 6 and 7, respectively.

For example, the immunoglobulin or antibody comprises:
(i) a $V_L$ comprising:
   a) a CDR1 comprising a sequence set forth in SEQ ID NO: 2 (or encoded by a sequence set forth in SEQ ID NO: 14);
   b) a CDR2 comprising a sequence set forth in SEQ ID NO: 3 (or encoded by a sequence set forth in SEQ ID NO: 15); and
   c) a CDR3 comprising a sequence set forth in SEQ ID NO: 4 (or encoded by a sequence set forth in SEQ ID NO: 16); and
(ii) a $V_H$ comprising:
   d) a CDR1 comprising a sequence set forth in SEQ ID NO: 5 (or encoded by a sequence set forth in SEQ ID NO: 17);
   e) a CDR2 comprising a sequence set forth in SEQ ID NO: 6 (or encoded by a sequence set forth in SEQ ID NO: 18); and
   f) a CDR3 comprising a sequence set forth in SEQ ID NO: 7 (or encoded by a sequence set forth in SEQ ID NO: 19).

The present disclosure additionally or alternatively provides an isolated or recombinant humanized antibody or antigen binding fragment thereof, the antibody or antigen binding fragment capable of specifically binding to IL-3Rα chain and comprising a $V_L$ comprising an amino acid sequence according to SEQ ID NO: 8 (or encoded by a sequence set forth in SEQ ID NO: 20) and/or a $V_H$ comprising an amino acid sequence according to SEQ ID NO: 9 (or encoded by a sequence set forth in SEQ ID NO: 21).

The present disclosure additionally or alternatively provides an isolated or recombinant humanized antibody or antigen binding fragment thereof, the antibody or antigen binding fragment capable of specifically binding to IL-3Rα chain and comprising a $V_L$ comprising an amino acid sequence according to SEQ ID NO: 8 (or encoded by a sequence set forth in SEQ ID NO: 20) and a $V_H$ comprising an amino acid sequence according to SEQ ID NO: 9 (or encoded by a sequence set forth in SEQ ID NO: 21).

Exemplary antigen binding fragments contemplated by the present disclosure include:
(i) a domain antibody (dAb);
(ii) a Fv;
(iii) a scFv or stabilized form thereof (e.g., a disulfide stabilized scFv);
(iv) a dimeric scFv or stabilized form thereof;
(v) a diabody, triabody, tetrabody or higher order multimer;
(vi) Fab fragment;
(vii) a Fab' fragment;
(viii) a F(ab') fragment;
(ix) a F(ab')$_2$ fragment;
(x) any one of (i)-(ix) fused to a Fc region of an antibody;
(xi) any one of (i)-(ix) fused to an antibody or antigen binding fragment thereof that binds to an immune effector cell.

In one example, the immunoglobulin or antibody depletes or at least partly eliminates cells to which it binds, e.g., leukemic cells and/or basophils and/or pDCs.

As will be apparent to the skilled artisan from the disclosure herein, exemplary immunoglobulins or antibodies are capable of depleting or at least partly eliminating cells to which it binds without being conjugated to a toxic compound.

In one example, the immunoglobulin or antibody is capable of inducing an effector function, e.g., an effector function that results in killing a cell to which the immunoglobulin or antibody binds. Exemplary effector functions include ADCC, antibody-dependent cell-mediated phagocytosis (ADCP) and/or complement-dependent cytotoxicity (CDC).

In one example, the immunoglobulin or antibody is capable of inducing ADCC.

In one example, the immunoglobulin or antibody comprises an antibody Fc region capable of inducing an effector function. For example, the effector function is Fc-mediated effector function. In one example, the Fc region is an IgG1 Fc region or an IgG3 Fc region or a hybrid IgG1/IgG2 Fc region.

In one example, the immunoglobulin or antibody is capable of inducing a similar (e.g., not significantly different or within about 10%) or the same level of effector function as a wild-type human IgG1 and/or human IgG3 Fc region.

In one example, the immunoglobulin or antibody is capable of inducing an enhanced level of effector function.

In one example, the level of effector function induced by the immunoglobulin or antibody is enhanced relative to that of the immunoglobulin or antibody when it comprises a wild-type IgG1 Fc region.

In one example the immunoglobulin or antibody is afucosylated or comprises a Fc region that is afucosylated.

In another example, the immunoglobulin or antibody has a lower level of fucosylation compared to an immunoglobulin or antibody produced by a human or a CHO cell that has not been altered to reduce the level of fucosylation of proteins.

In accordance with this example, a lower level of fucosylation will be understood to mean that in a composition comprising the immunoglobulin or antibody the percentage of fucosylated immunoglobulins (e.g., glycosyl groups attached to Asn297 of an antibody comprising fucose) is lower than produced by a human or a CHO cell that has not been altered to reduce the level of fucosylation of proteins.

For example, the immunoglobulin or antibody is an afucosylated humanized antibody comprising a $V_L$ comprising a sequence set forth in SEQ ID NO: 8 (or encoded by a sequence set forth in SEQ ID NO: 20) and a $V_H$ comprising a sequence set forth in SEQ ID NO: 9 (or encoded by a sequence set forth in SEQ ID NO: 21). For example, the immunoglobulin or antibody is an afucosylated humanized antibody comprising a light chain comprising a sequence set forth in SEQ ID NO: 13 (or encoded by a sequence set forth in SEQ ID NO: 23) and a heavy chain comprising a sequence set forth in SEQ ID NO: 10 (or encoded by a sequence set forth in SEQ ID NO: 22).

In one example, the immunoglobulin or antibody is a humanized antibody comprising a light chain comprising a sequence set forth in SEQ ID NO: 13 (or encoded by a sequence set forth in SEQ ID NO: 23) and a heavy chain comprising a sequence set forth in SEQ ID NO: 10 (or encoded by a sequence set forth in SEQ ID NO: 22) expressed by a mammalian cell (e.g., a CHO cell) that does not express detectable levels of (or expresses reduced levels of) α-1,6-fucosyltransferase (FUT8).

In one example, the immunoglobulin or antibody comprises an Fc region comprising one or more amino acid sequence substitutions that enhance the effector function induced by the immunoglobulin. For example, the one or more amino acid sequence substitutions increase the affinity of the Fc region for a Fcγ receptor (FcγR) compared to a Fc region not comprising the substitutions. For example, the one or more amino acid substitutions enhance increase the affinity of the Fc region for a FcγR selected from the group consisting of FcγRI, FcγRIIa, FcγRIIc and FcγRIIIa compared to a Fc region not comprising the substitutions. In one example, the one or more amino acid sequence substitutions are:
(i) S239D, A330L and I332E according to the EU numbering system of Kabat; or
(ii) S239D and I332E according to the EU numbering system of Kabat.

For example, the immunoglobulin or antibody is a humanized antibody comprising a $V_L$ comprising a sequence set forth in SEQ ID NO: 8 (or encoded by a sequence set forth in SEQ ID NO: 20) and a $V_H$ comprising a sequence set forth in SEQ ID NO: 9 (or encoded by a sequence set forth in SEQ ID NO: 21), wherein the antibody comprises a Fc region comprising one or more amino acid sequence substitutions selected from the group consisting of:
(i) S239D, A330L and I332E according to the EU numbering system of Kabat; and
(ii) S239D and I332E according to the EU numbering system of Kabat.

In one example, the Fc region comprises a sequence set forth between residues 234-450 of SEQ ID NO: 11 (comprising the S239D and I332E substitutions according to the EU numbering system of Kabat).

In one example, the Fc region comprises a sequence set forth between residues 234-450 of SEQ ID NO: 12 (comprising the S239D, A330L and I332E substitutions according to the EU numbering system of Kabat).

In one example, the immunoglobulin or antibody is selected from the group consisting of:
(i) an antibody comprising a light chain comprising a sequence set forth in SEQ ID NO: 13 and a heavy chain comprising a sequence set forth in SEQ ID NO: 11;
(ii) an antibody comprising a comprising a light chain comprising a sequence set forth in SEQ ID NO: 13 and a heavy chain comprising a sequence set forth in SEQ ID NO: 12.

As discussed herein above, the inventor has determined that following administration of an antibody described herein, the number of NK cells in circulation in a mammal are initially reduced and then increased compared to the number of NK cells in circulation in the mammal prior to administration. The inventor has also shown that increasing the number of NK cells relative to target cells results in increased efficacy, i.e., a greater number of target cells are killed. This effect is induced by an antibody comprising a constant region or Fc region comprising amino acid substitutions S239D and I332E according to the EU numbering system of Kabat.

Thus, in one example, the present disclosure provides an isolated or recombinant antibody, which is capable of specifically binding to IL-3Rα chain and comprising:
(i) a light chain variable region ($V_L$) comprising CDRs 1, 2 and 3 as set forth in SEQ ID NOs: 2, 3 and 4, respectively;
(ii) a heavy chain variable region ($V_H$) comprising CDRs 1, 2 and 3 as set forth in SEQ ID NOs: 5, 6 and 7, respectively; and
(iii) a heavy chain constant region comprising amino acid substitutions S239D and I332E according to the EU numbering system of Kabat.

In one example, the present disclosure provides an isolated or recombinant humanized antibody, the antibody capable of specifically binding to IL-3Rα chain and comprising:
(i) a $V_L$ comprising:
   a) a CDR1 comprising a sequence set forth in SEQ ID NO: 2 (or encoded by a sequence set forth in SEQ ID NO: 14);
   b) a CDR2 comprising a sequence set forth in SEQ ID NO: 3 (or encoded by a sequence set forth in SEQ ID NO: 15); and
   c) a CDR3 comprising a sequence set forth in SEQ ID NO: 4 (or encoded by a sequence set forth in SEQ ID NO: 16);
(ii) a $V_H$ comprising:
   d) a CDR1 comprising a sequence set forth in SEQ ID NO: 5 (or encoded by a sequence set forth in SEQ ID NO: 17);
   e) a CDR2 comprising a sequence set forth in SEQ ID NO: 6 (or encoded by a sequence set forth in SEQ ID NO: 18); and
   f) a CDR3 comprising a sequence set forth in SEQ ID NO: 7 (or encoded by a sequence set forth in SEQ ID NO: 19); and
(iii) a heavy chain constant region comprising amino acid substitutions S239D and I332E according to the EU numbering system of Kabat.

In one example, the heavy chain constant region is a hybrid of a human IgG1 and a human IgG2 constant regions.

In one example, the constant region comprises a sequence set forth between residues 121-450 (inclusive) of SEQ ID NO: 11.

The present disclosure additionally or alternatively provides an isolated or recombinant humanized antibody, the antibody capable of specifically binding to IL-3Rα chain and comprising:
(i) a $V_L$ comprising an amino acid sequence according to SEQ ID NO: 8 (or encoded by a sequence set forth in SEQ ID NO: 20) and/or a $V_H$ comprising an amino acid sequence according to SEQ ID NO: 9 (or encoded by a sequence set forth in SEQ ID NO: 21); and
(ii) a heavy chain constant region comprising amino acid substitutions S239D and I332E according to the EU numbering system of Kabat.

In one example, the heavy chain constant region is a hybrid of a human IgG1 and a human IgG2 constant regions.

In one example, the constant region comprises a sequence set forth between residues 121-450 (inclusive) of SEQ ID NO: 11.

The present disclosure additionally or alternatively provides an isolated or recombinant humanized antibody, the antibody capable of specifically binding to IL-3Rα chain and comprising a $V_L$ comprising an amino acid sequence according to SEQ ID NO: 8 (or encoded by a sequence set forth in SEQ ID NO: 20), a $V_H$ comprising an amino acid sequence according to SEQ ID NO: 9 (or encoded by a sequence set forth in SEQ ID NO: 21) and a heavy chain constant region comprising amino acid substitutions S239D and I332E according to the EU numbering system of Kabat.

In one example, the heavy chain constant region is a hybrid of a human IgG1 and a human IgG2 constant regions.

In one example, the constant region comprises a sequence set forth between residues 121-450 (inclusive) of SEQ ID NO: 11

In one example, the present disclosure provides an isolated or recombinant humanized antibody, the antibody capable of specifically binding to IL-3Rα chain and comprising a light chain comprising a sequence set forth in SEQ ID NO: 13 and a heavy chain comprising a sequence set forth in SEQ ID NO: 11.

In one example, an immunoglobulin or antibody or antigen binding fragment thereof of the present disclosure neutralizes IL-3 signaling.

In one example, an immunoglobulin or antibody of the present disclosure is a naked immunoglobulin or an antibody or antigen binding fragment thereof of the present disclosure is a naked antibody or antigen binding fragment thereof.

In one example, an immunoglobulin or antibody of the present disclosure is a full length antibody.

In one example, an immunoglobulin or antibody of the present disclosure binds to IL-3Rα chain with an equilibrium dissociation constant ($K_D$) of $1 \times 10^{-8}$M or less, such as $5 \times 10^{-9}$M or less, for example, $3 \times 10^{-9}$M or less, such as $2.5 \times 10^{-9}$M or less.

In one example, an immunoglobulin or antibody of the present disclosure binds to IL-3Rα chain with a $K_D$ of about $2.2 \times 10^{-9}$M or less. In one example, the $K_D$ is between about $1 \times 10^{-9}$M and about $2.5 \times 10^{-9}$M, for example is about $2.2 \times 10^{-9}$M.

In one example, an immunoglobulin or antibody of the present disclosure binds to IL-3Rα chain with a $K_D$ of about $9 \times 10^{-10}$M or less, for example, about $8 \times 10^{-10}$M or less. In one example, the $K_D$ is between about $5 \times 10^{-10}$M and about $9 \times 10^{-10}$M, for example is about $7.8 \times 10^{-10}$M.

The disclosure also includes fragments, variants and derivatives of the immunoglobulin or antibody of the disclosure.

In one example, an immunoglobulin or antibody of the present disclosure is capable of reducing the number of NK cells when administered to a mammal (e.g., a non-human primate, such as a cynomolgus monkey). For example, the immunoglobulin or antibody is capable of reducing the number of NK cells when administered to the mammal by at least about 20%, such as at least about 30% or 40% within 12 hours or 10 hours or 8 hours of administration. For example, the immunoglobulin or antibody is capable of reducing the number of NK cells when administered to the mammal by at least about 50% within 6 hours of administration. In one example, the immunoglobulin or antibody is capable of reducing the number of NK cells when administered at a dose of between 0.0001 mg/kg and 50 mg/kg, such as between about 0.0005 mg/kg and about 40 mg/kg, for example, between about 0.001 mg/kg and about 30 mg/kg, such as about 0.005 mg/kg and about 20 mg/kg, such as about 0.01 mg/kg and about 10 mg/kg. For example, the immunoglobulin or antibody is capable of reducing the number of NK cells when administered to the mammal by at least about 50% within 6 hours of administration when administered at a dose of about 0.01 mg/kg or 0.1 mg/kg or 1 mg/kg or 10 mg/kg. In one example, the dose is about 0.01 mg/kg or 0.1 mg/kg.

In one example, the number of NK cells in the mammal is increased about 7 or 8 or 9 or 10 or 11 or 12 or 13 or 14 or 15 or 16 or 17 or 18 or 19 or 20 or 22 or 29 or 57 days after administering the immunoglobulin or antibody compared to the number of NK cells in the mammal prior to administration of the immunoglobulin or antibody. For example, the number of NK cells is increased at least about 8 or 11 or 17 or 22 or 29 days after administration. For example, the number of NK cells in the mammal is increased by about 10% or 20% or 30% or 50% or 60% or 70% or 80% compared to the number of NK cells in the mammal prior to administration of the immunoglobulin or antibody. For example, the number of NK cells in the mammal is increased by about 20% at least 8 days after administration of the antibody or immunoglobulin at a dose between 0.001 mg/kg and 0.1 mg/kg compared to the number of NK cells in the mammal prior to administration of the immunoglobulin or antibody. For example, the number of NK cells in the mammal is increased by about 50% at least 11, 17, 22 or 29 days after administration of the antibody or immunoglobulin at a dose between 0.001 mg/kg and 0.1 mg/kg compared to the number of NK cells in the mammal prior to administration of the immunoglobulin or antibody. In one example, the antibody or immunoglobulin is administered at a dose of between 0.01 mg/kg and 0.1 mg/kg. For example, the immunoglobulin or antibody is administered at a dose of 0.01 mg/kg or 0.1 mg/kg.

Based on the disclosure herein, it will be apparent to the skilled artisan that the present disclosure provides an immunoglobulin or antibody that, when administered to a mammal, causes an increase in the number of NK cells in the mammal. For example, the immunoglobulin or antibody, when administered to a mammal, causes a reduction in the number of NK cells in the mammal followed by an increase in the number of NK cells. In one example, the number of NK cells is increased or reduced compared to the number of NK cells in the mammal prior to administration of the immunoglobulin or antibody.

In one example, the immunoglobulin or antibody is capable of reducing the number of NK cells in the mammal by at least about 50% within 6 hours of administration when administered at a dose of about 0.01 mg/kg or 0.1 mg/kg and the number of NK cells in the mammal is increased by about 20% at least 8 days after administration of the antibody or immunoglobulin at a dose between 0.001 mg/kg and 0.1 mg/kg compared to the number of NK cells in the mammal prior to administration of the immunoglobulin or antibody.

In one example, the disclosure provides a pharmaceutical composition comprising an immunoglobulin or antibody according to the present disclosure and a pharmaceutically acceptable carrier, diluent or excipient.

The present disclosure also provides an isolated nucleic acid encoding an immunoglobulin or antibody of the present disclosure.

Exemplary sequences of nucleic acids are discussed in the context of encoding antibodies or immunoglobulins of the disclosure and are to be taken to apply mutatis mutandis to the present example of the disclosure.

The present disclosure also provides a nucleic acid capable of hybridizing to a nucleic acid of the disclosure under high stringency hybridization conditions.

The disclosure also includes fragments, homologs and derivatives of an isolated nucleic acid of the disclosure.

The present disclosure also provides a genetic construct comprising an isolated nucleic acid of the disclosure and one or more additional nucleotide sequences, such as a promoter operably linked to the nucleic acid.

In one example, the genetic construct is an expression construct comprising an expression vector and an isolated nucleic acid of the disclosure, wherein said isolated nucleic acid is operably linked to one or more regulatory nucleic acids in said expression vector.

In one example, the genetic construct of the disclosure comprises a nucleic acid encoding a polypeptides (e.g., comprising a $V_H$) operably linked to a promoter and a nucleic acid encoding another polypeptide (e.g., comprising a $V_L$) operably linked to a promoter.

In another example, the genetic construct is a bicistronic genetic construct, e.g., comprising the following operably linked components in 5' to 3' order:

(i) a promoter (ii) a nucleic acid encoding a first polypeptide;

(iii) an internal ribosome entry site; and (iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate genetic constructs one of which encodes a first polypeptide (e.g., comprising a $V_H$) and another of which encodes a second polypeptide (e.g., comprising a $V_L$). For example, the present disclosure also provides a composition comprising:

(i) a first expression construct comprising a nucleic acid encoding a polypeptide (e.g., comprising a $V_H$) operably linked to a promoter; and (ii) a second expression construct comprising a nucleic acid encoding a polypeptide (e.g., comprising a $V_L$) operably linked to a promoter.

The disclosure also provides a host cell comprising a genetic construct according to the present disclosure.

In one example, the present disclosure provides an isolated cell expressing an immunoglobulin or antibody or antigen binding fragment of the disclosure or a recombinant cell genetically-modified to express the immunoglobulin, antibody or antigen binding fragment.

In one example, the cell comprises the genetic construct of the disclosure or:
(i) a first genetic construct comprising a nucleic acid encoding a polypeptide (e.g., comprising a $V_H$) operably linked to a promoter; and
(ii) a second genetic construct comprising a nucleic acid encoding a polypeptide (e.g., comprising a $V_L$) operably linked to a promoter,
wherein the first and second polypeptides form an immunoglobulin, antibody or antigen binding fragment of the present disclosure.

The genetic construct can be integrated into the cell or remain episomal.

Examples of cells of the present disclosure include bacterial cells, yeast cells, insect cells or mammalian cells.

The present disclosure additionally provides a method for producing an immunoglobulin, antibody or antigen binding fragment of the disclosure, the method comprising maintaining the genetic construct(s) of the disclosure under conditions sufficient for the immunoglobulin, antibody or antigen binding fragment to be produced.

In one example, the method for producing an immunoglobulin, antibody or antigen binding fragment of the disclosure comprises culturing the cell of the disclosure under conditions sufficient for the immunoglobulin, antibody or antigen binding fragment to be produced and, optionally, secreted.

In one example, the method for producing an immunoglobulin, antibody or antigen binding fragment of the disclosure additionally comprises isolating the immunoglobulin, antibody or antigen binding fragment.

The present disclosure additionally provides a method of producing a recombinant immunoglobulin or antibody of the disclosure, the method including the steps of:
(i) culturing a host cell containing an expression vector according to the disclosure such that the recombinant immunoglobulin or antibody is expressed in said host cell; and
(ii) isolating the recombinant immunoglobulin.

In one example, a method for producing an immunoglobulin, antibody or antigen binding fragment of the disclosure additionally comprises formulating the immunoglobulin, antibody or antigen binding fragment with a pharmaceutically acceptable carrier.

The present disclosure also provides a method of prophylactic or therapeutic treatment of a disease or condition in a mammal, the method including the step of administering the immunoglobulin or antibody of the disclosure to the mammal to thereby treat or prevent the disease or condition.

In one example, the mammal is a human.

In one example, the mammal is in need of treatment or prophylaxis.

In one example, the mammal in need suffers from the disease or condition.

In one example, the mammal in need is at risk of developing the disease or condition or a relapse thereof.

The present disclosure also provides for use of an immunoglobulin, antibody or antigen binding fragment of the disclosure or a composition of the disclosure in medicine.

The present disclosure additionally or alternatively provides for use of an immunoglobulin, antibody or antigen binding fragment of the disclosure in the manufacture of a medicament for the treatment of a disease or condition in a mammal.

The present disclosure also provides an immunoglobulin, antibody or antigen binding fragment of the disclosure for use in the treatment of a disease or condition in a mammal.

In one example, the disease or condition is an IL-3Rα-mediated disease or condition.

In one example, the disease or condition is myelodysplastic syndrome.

In one example, the disease or condition is cancer, such as a hematologic cancer, for example, leukemia, such as an acute leukemia (e.g., acute myelogenous leukemia) or a chronic leukemia (e.g., chronic myelomonocytic leukemia).

In one example, the disease or condition is an IL-3Rα-associated cancer, e.g., leukemia, i.e., the cancer (or leukemia) is characterized by cancer (or leukemia) cells expressing IL-3Rα.

In another example, the cancer is a malignant lymphoproliferative disorder such as lymphoma.

In one example, the disease or condition is an autoimmune condition or an inflammatory condition. For example, the condition is lupus, e.g., systemic lupus erythrematosus, Sjögren's syndrome or scleroderma (e.g., systemic scleroderma).

In one example, the method comprises administering an effective amount of the immunoglobulin, such as a therapeutically effective amount of the immunoglobulin, antibody or antigen binding fragment.

In one example, the method comprises administering between about 0.0001 mg/kg and 50 mg/kg of immunoglobulin, antibody or antigen binding fragment to the mammal. For example, the method comprises administering between about 0.0005 mg/kg to about 40 mg/kg. For example, the method comprises administering between about 0.0005 mg/kg to about 30 mg/kg. For example, the method comprises administering between about 0.001 mg/kg to about 20 mg/kg. For example, the method comprises administering between about 0.001 mg/kg to about 10 mg/kg. For example, the method comprises administering between about 0.01 mg/kg to about 5 mg/kg. For example, the method comprises administering between about 0.001 mg/kg to about 1 mg/kg.

In one example, the method comprises administering between about 0.1 mg/kg to about 10 mg/kg of the immunoglobulin, antibody or antigen binding fragment. For example, the method comprises administering between about 0.1 mg/kg to about 5 mg/kg. For example, the method comprises administering between about 0.1 mg/kg to about 1 mg/kg.

In one example, the method comprises administering between about 10 mg/kg to about 30 mg/kg of the immunoglobulin, antibody or antigen binding fragment. For example, the method comprises administering between about 20 mg/kg to about 30 mg/kg.

In one example, the immunoglobulin, antibody or antigen binding fragment is administered at a dose of 0.01 mg/kg.

In one example, the immunoglobulin, antibody or antigen binding fragment is administered at a dose of 0.1 mg/kg.

In one example, the immunoglobulin, antibody or antigen binding fragment is administered at a dose of 1 mg/kg.

In one example, the immunoglobulin, antibody or antigen binding fragment is administered at a dose of 10 mg/kg.

In one example, the immunoglobulin, antibody or antigen binding fragment is administered at a dose of 30 mg/kg.

In one example, the immunoglobulin or antibody is administered to the mammal a plurality of times. In one example, the period between administrations is at least about 7 days, such as at least about 8 days, for example, at least about 9 days or 10 days. In one example, the period between administrations is at least about 11 days. In another example, the period between administrations is at least about 15 days, such as at least about 16 days, for example, at least about 18 days or 20 days. In one example, the period between administrations is at least about 22 days. In another example, the period between administrations is at least about 25 days, such as at least about 30 days, for example, at least about 40 days or 45 days. In one example, the period between administrations is at least about 57 or 60 days.

For example, the immunoglobulin, antibody or antigen binding domain is administered at a dose of between 0.0001 mg/kg and 5 mg/kg, such as between 0.0005 mg/kg and 5 mg/kg, for example, between 0.001 mg/kg and 5 mg/kg, and the period between administrations is at least about 7 days or 8 days or 9 days or 10 days or 11 days or 14 days or 17 days or 21 days or 22 days or 28 days or 29 days or 30 days or 1 calendar month. For example, the immunoglobulin, antibody or antigen binding domain is administered at a dose of between 0.01 mg/kg and 5 mg/kg and the period between administrations is at least about 7 days or 8 days or 9 days or 10 days or 11 days or 14 days. For example, the immunoglobulin, antibody or antigen binding domain is administered at a dose of between 0.01 mg/kg and 2 mg/kg and the period between administrations is at least about 7 days or 8 days or 9 days or 10 days or 11 days or 14 days. For example, the immunoglobulin, antibody or antigen binding domain is administered at a dose of between 0.01 mg/kg and 1 mg/kg and the period between administrations is at least about 7 days or 8 days or 9 days or 10 days or 11 days or 14 days. In some examples, the period between administrations is at least about 7 days and less than about 22 days, such as at least about 11 days or 15 days and less than about 20 days, for example at least about 13 days and less than about 18 days.

In one example, the immunoglobulin, antibody or antigen binding domain is administered at a dose of 0.01 mg/kg and the period between administrations is 6 days or 7 days or 8 days or 9 days or 10 days or 11 days or 14 days or 15 days.

In one example, the immunoglobulin, antibody or antigen binding domain is administered at a dose of 0.1 mg/kg and the period between administrations is 6 days or 7 days or 8 days or 9 days or 10 days or 11 days or 14 days or 15 days.

In one example, the immunoglobulin or antibody is administered at a dose of 1 mg/kg and the period between administrations is 6 days or 7 days or 8 days or 9 days or 10 days or 11 days or 14 days or 15 days or 20 days or 21 days or 22 days.

For example, the immunoglobulin or antibody is administered at a dose of between 6 mg/kg and 50 mg/kg and the period between administrations is at least about 15 days. For example, the immunoglobulin or antibody is administered at a dose of between 10 mg/kg and 30 mg/kg and the period between administrations is at least about 14 or 15 days. For example, the immunoglobulin or antibody is administered at a dose of between 20 mg/kg and 30 mg/kg and the period between administrations is at least about 14 or 15 days. In some examples, the period between administrations is at least about 20 days and less than about 70 days, such as at least about 21 or 22 days and less than about 65 days, for example at least about 25 days and less than about 57 days.

In one example, the immunoglobulin or antibody is administered at a dose of 10 mg/kg and the period between administrations is 14 days or 15 days or 21 days or 22 days or 30 days or 48 days or 50 days or 56 days or 57 days or 60 days.

In one example, the immunoglobulin or antibody is administered at a dose of 30 mg/kg and the period between administrations is 14 days or 15 days or 21 days or 22 days or 30 days or 48 days or 50 days or 56 days or 57 days or 60 days.

As discussed above, the inventor has found that following administration of an immunoglobulin or antibody of the disclosure the number of NK cells is increased above the number present before administration within about 8 days. The inventor has also shown that increased numbers of NK cells increase the efficacy of an antibody or immunoglobulin of the disclosure in inducing death of target cells. Thus, once the number of NK cells is increased, a further dose of the antibody or immunoglobulin can be administered to induce a therapeutic/prophylactic effect. For example, an immunoglobulin, antibody or antigen binding fragment of the disclosure is administered a plurality of times at a dose of between about 0.001 mg/kg and about 1 mg/kg with a period between administrations of at least about 7 days, such as, at least about 8 days, for example, at least about 11 days, such as at least about 14 days, for example, at least about 17 days, such as at least about 21 days, for example, at least about 22 days, for example, 28 days or 29 days or one calendar month or 56 or 57 or 60 days. In one example, the period between doses is about 7 days. In one example, the period between doses is about 8 days. In one example, the period between doses is about 11 days. In one example, the period between doses is about 14 days. In one example, the period between doses is about 17 days. In one example, the period between doses is about 21 days. In one example, the period between doses is about 22 days. In one example, the period between doses is about 28 days. In one example, the period between doses is about 29 days. In one example, the dose is between about 0.01 mg/kg and about 0.1 mg/kg, such as a dose of about 0.01 mg/kg or 0.1 mg/kg.

DETAILED DESCRIPTION

Figure 1A:
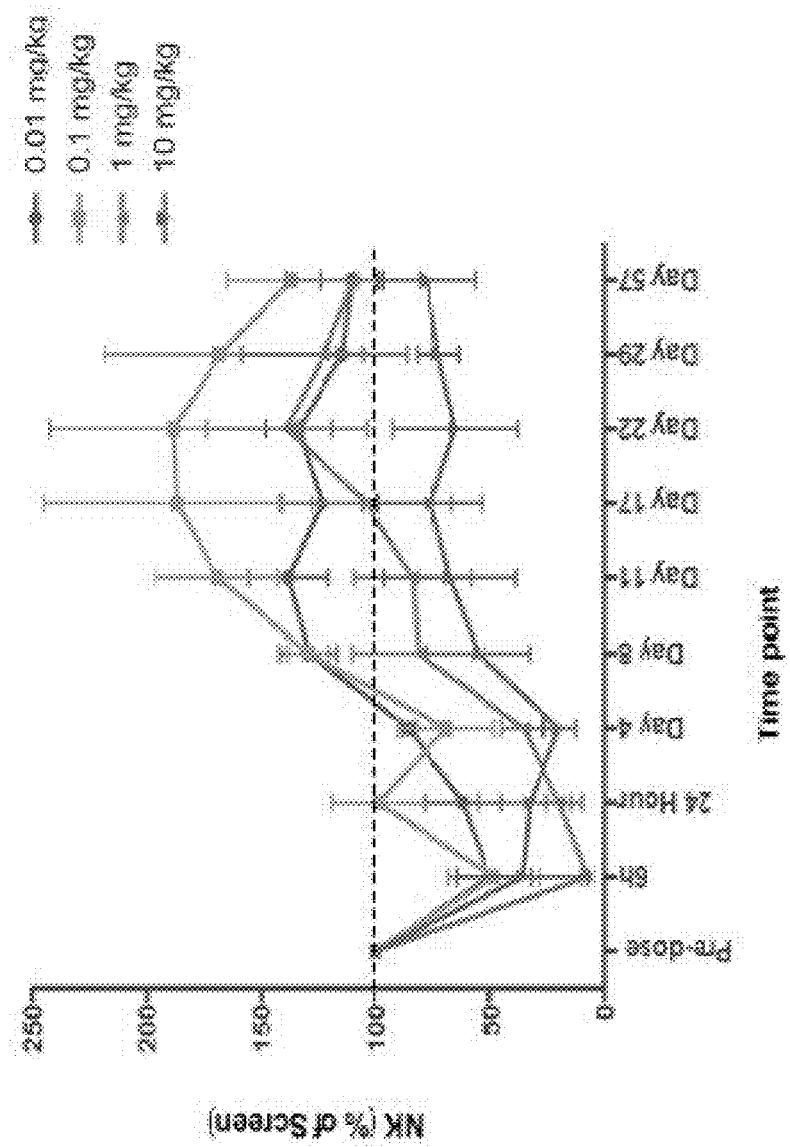
FIG. 1A is a graphical representation showing the number of NK cells in a sample from a non-human primate subject at various time points (as indicated) following administration of antibody CSL362×2. The number of cells is represented as a percentage of the number of cells prior to administering the antibody. Dosages of the antibody are indicated.

Key to Sequence Listing
SEQ ID NO: 1—amino acid sequence of IL-3Rα chain
SEQ ID NO: 2—amino acid sequence of LCDR1 of humanized anti-IL-3Rα chain antibody CSL362 and modified forms thereof
SEQ ID NO: 3—amino acid sequence of LCDR2 of humanized anti-IL-3Rα chain antibody CSL362 and modified forms thereof SEQ ID NO: 4—amino acid sequence of LCDR3 of humanized anti-IL-3Rα chain antibody CSL362 and modified forms thereof SEQ ID NO: 5—amino acid sequence of HCDR1 of humanized anti-IL-3Rα chain antibody CSL362 and modified forms thereof SEQ ID NO: 6—amino acid sequence of HCDR2 of humanized anti-IL-3Rα chain antibody CSL362 and modified forms thereof SEQ ID NO: 7—amino acid sequence of HCDR3 of humanized anti-IL-3Rα chain antibody CSL362 and modified forms thereof SEQ ID NO: 8—amino acid sequence of light chain variable region of humanized anti-IL-3Rα chain antibody CSL362 and modified forms thereof SEQ ID NO: 9—amino acid sequence of heavy chain variable region of humanized anti-IL-3Rα chain antibody CSL362 and modified forms thereof.

SEQ ID NO: 10—amino acid sequence of heavy chain of humanized anti-IL-3Rα chain antibody CSL362 and CSL362B SEQ ID NO: 11—amino acid sequence of heavy chain of humanized anti-IL-3Rα chain antibody CSL362X1

SEQ ID NO: 12—amino acid sequence of heavy chain of humanized anti-IL-3Rα chain antibody CSL362X2

SEQ ID NO: 13—amino acid sequence of light chain of humanized anti-IL-3Rα chain antibody CSL362 and modified forms thereof SEQ ID NO: 14—nucleotide sequence encoding a LCDR1 of humanized anti-IL-3Rα chain antibody CSL362 and modified forms thereof.

SEQ ID NO: 15—nucleotide sequence encoding a LCDR2 of humanized anti-IL-3Rα chain antibody CSL362 and modified forms thereof SEQ ID NO: 16—nucleotide sequence encoding a LCDR3 of humanized anti-IL-3Rα chain antibody CSL362 and modified forms thereof SEQ ID NO: 17—nucleotide sequence encoding a HCDR1 of humanized anti-IL-3Rα chain antibody CSL362 and modified forms thereof SEQ ID NO: 18—nucleotide sequence encoding a HCDR2 of humanized anti-IL-3Rα chain antibody CSL362 and modified forms thereof SEQ ID NO: 19—nucleotide sequence encoding a HCDR3 of humanized anti-IL-3Rα chain antibody CSL362 and modified forms thereof.

SEQ ID NO: 20—nucleotide sequence encoding a light chain variable region of humanized anti-IL-3Rα chain antibody CSL362 and modified forms thereof SEQ ID NO: 21—nucleotide sequence encoding a heavy chain variable region of humanized anti-IL-3Rα chain antibody CSL362 and modified forms thereof SEQ ID NO: 22—nucleotide sequence encoding a heavy chain of humanized anti-IL-3Rα chain antibody CSL362 and CSL362B SEQ ID NO: 23—nucleotide sequence encoding a light chain of humanized anti-IL-3Rα chain antibody CSL362 and modified forms thereof.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

SELECTED DEFINITIONS

As used herein, the term "immunoglobulin" includes any antigen-binding protein product of the immunoglobulin gene complex, including immunoglobulin isotypes IgA, IgD, IgM, IgG and IgE and antigen-binding fragments thereof. Exemplary immunoglobulins are antibodies. Exemplary immunoglobulins are monoclonal. Included in the term "immunoglobulin" are any immunoglobulins that are appropriately de-immunized to thereby reduce or eliminate an immune response by a mammal to an immunoglobulin that has been administered to the mammal. In the case of treatment of humans, suitable immunoglobulins include chimeric, humanized or human immunoglobulins. Also included within the term "immunoglobulin" are modified, mutagenized, chimeric and/or humanized immunoglobulins that comprise altered or variant amino acid residues, sequences or glycosylation, whether naturally occurring or produced by human intervention (e.g. by recombinant DNA technology). Exemplary proteins include an Fc receptor binding portion. For example, proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors and other immunoglobulin-like domain containing proteins that are capable of binding to an antigen, e.g., by virtue of an antigen binding site comprising a variable region.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" encompasses humanized antibodies.

The term "humanized antibody" shall be understood to refer to an antibody comprising a human-like variable region including CDRs from an antibody from a non-human species (e.g., mouse) grafted onto or inserted into FRs from a human antibody (this type of antibody is also referred to a "CDR-grafted antibody"). Humanized antibodies also include antibodies in which one or more residues of the human antibody are modified by one or more amino acid substitutions and/or one or more FR residues of the human protein are replaced by corresponding non-human residues. As exemplified herein, humanized antibodies may also comprise residues which are found in neither the human antibody or in the non-human antibody. Any additional regions of the antibody (e.g., Fc region) are generally human. Humanization can be performed using a method known in the art, e.g., U.S. Pat. No. 5,225,539, U.S. Pat. No. 6,054,297, U.S. Pat. No. 7,566,771 or U.S. Pat. No. 5,585,089. The term "humanized antibody" also encompasses a super-humanized protein, e.g., as described in U.S. Pat. No. 7,732,578.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof. In some cases, the intact antibody may be capable of inducing one or more effector functions.

The term "naked antibody" refers to an antibody that is not conjugated to another compound, e.g., a toxic compound or radiolabel.

An "antigen binding fragment" of an antibody comprises the antigen binding domain and/or the variable region of the intact antibody. Examples of antibody fragments include Fab, Fab', $F(ab)_2$ and Fv fragments; diabodies; linear antibodies; single-chain antibody molecules and multispecific antibodies formed from antibody fragments.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies or immunoglobulins include: complement dependent cytotoxicity; antibody-dependent-cell-mediated cytotoxicity (ADCC); antibody-dependent-cell-phagocytosis (ADCP); and B-cell activation. In the context of the present disclosure, the term or "effector function induced by an antibody" or like term is used interchangeably with "effector function of an immunoglobulin" or "effector function of an antibody" or like term and each provides literal support for the other.

"Antibody-dependent-cell-mediated cytotoxicity" or "ADCC" refers to a form of cytotoxicity in which secreted Ig bound onto Fc receptors ("FcRs") present on certain cytotoxic cells (e.g., natural killer ("NK") cells, neutrophils and macrophages) enable these cytotoxic effector cells to bind specifically to an antigen-bearing target-cell and subsequently kill the target-cell with cytotoxins. To assess ADCC activity of a molecule of interest, an in vitro ADCC assay may be performed. Useful effector cells for such assays include peripheral blood mononuclear cells ("PBMC") and NK cells.

As used herein, "variable region" refers to the portions of the light and/or heavy chains of an antibody as defined herein that is capable of specifically binding to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat *Sequences of Proteins of Immunological Interest*, National Institutes of Health, Bethesda, Md., 1987 and 1991 (also referred to herein as "the Kabat numbering system". According to the numbering system of Kabat, $V_H$ FRs and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4).

"Framework regions" (hereinafter FR) are those variable domain residues other than the CDR residues.

The term "constant region" as used herein, refers to a portion of heavy chain or light chain of an antibody other than the variable region. In a heavy chain, the constant region generally comprises a plurality of constant domains and a hinge region, e.g., a IgG constant region comprises the following linked components, a constant heavy ($C_H$)1, a linker, a $C_H$2 and a $C_H$3. In a heavy chain, a constant region comprises a Fc. In a light chain, a constant region generally comprise one constant domain (a $C_L$1).

The term "fragment crystallizable" or "Fc" or "Fc region" or "Fc portion" (which can be used interchangeably herein) refers to a region of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α or δ heavy chain comprises two constant domains.

As used herein, the term "specifically binds" shall be taken to mean an immunoglobulin or antibody by which is meant that the binding interaction between an immunoglobulin or antibody and IL-3Rα chain is dependent on the presence of the antigenic determinant or epitope of an IL-3Rα chain bound by the immunoglobulin or antibody. Accordingly, the immunoglobulin or antibody preferentially binds or recognizes an IL-3Rα chain antigenic determinant or epitope even when present in a mixture of other molecules or organisms. In one example, the immunoglobulin or antibody reacts or associates more frequently, more rapidly, with greater duration and/or with greater affinity with IL-3Rα or cell expressing same than it does with alternative antigens or cells. It is also understood by reading this definition that, for example, an immunoglobulin or antibody specifically binds to IL-3Rα may or may not specifically bind to a second antigen. As such, "specific binding" does not necessarily require exclusive binding or non-detectable binding of another antigen. The term "specifically binds" is used interchangeably with "selectively binds" herein. Generally, reference herein to binding means specific binding, and each term shall be understood to provide explicit support for the other term. "In one example, "specific binding" to with IL-3Rα or cell expressing same, means that the immunoglobulin or antibody binds to the with IL-3Rα or cell expressing same with an equilibrium constant ($K_D$) of 100 nM or less, such as 50 nM or less, for example 20 nM or less, such as, 1 nM or less, e.g., 0.8 nM or less.

The term "EU numbering system of Kabat" will be understood to mean the numbering of an antibody heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

As used herein, the term "IL-3Rα-mediated condition" will be understood to mean a condition associated with or caused by excessive IL-3Rα expression and/or an excessive number of IL-3Rα expressing cells in a mammal, such as cancer cells (e.g., leukemic cells) and/or immune cells (e.g., plasmacytoid dendritic cells).

As used herein, the term "myelodysplastic syndrome" or "MDS" will be understood to refer to a diverse collection of hematological medical conditions that involve ineffective production (or dysplasia) of the myeloid class of blood cells. Subjects with MDS often develop severe anemia and can require frequent blood transfusions. In many cases, as MDS progresses the subject develops cytopenias (low blood counts) due to progressive bone marrow failure. In about one third of patients with MDS, the disease transforms into acute myelogenous leukemia (AML). The MDS can be diagnosed or classified to various systems, including the French-American-British Classification System (Bennett et al., *Br. J. Haematol.* 33: 451-458, 1976), The International Prognostic Scoring System (Greenberg et al., *Blood* 89: 2079-88, 1997) or a system published by the World Health Organization.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

As used herein, a mammal "at risk" of developing a disease or condition or relapse thereof or relapsing may or may not have detectable disease or symptoms of disease, and may or may not have displayed detectable disease or symptoms of disease prior to the treatment according to the present disclosure. "At risk" denotes that a mammal has one or more risk factors, which are measurable parameters that correlate with development of the disease or condition, as known in the art and/or described herein.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g., SLE). A therapeutically effective amount herein may vary according to factors such as the disease state, age, sex, and weight of the patient, and the ability of the immunoglobulin or antibody to elicit a desired response in the individual. A therapeutically effective amount is also one in which any toxic or detrimental effects of the immunoglobulin or antibody are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in mammals prior to or at an earlier stage of disease, a prophylactically effective amount may be less than a therapeutically effective amount.

Reference herein to "the number of NK cells in the mammal" will be understood to include the number of NK cells in a sample from a mammal and not to require determining the total number of NK cells in a mammal. This number can be expressed as, for example, cells per mL or dL or as a percentage of the number of cells from a sample taken at a different point in time from the mammal.

For the purposes of nomenclature only and not limitation, the amino acid sequence of an IL-3Rα chain is taught in Gene ID Accession Number 3563 and/or in SEQ ID NO: 1.

The "mammal" treated according to the present disclosure may be a mammal, such as a non-human primate or a human. In one example, the mammal is a human.

The term "sequence identity" is used herein in its broadest sense to include the number of exact nucleotide or amino acid matches having regard to an appropriate alignment using a standard algorithm, having regard to the extent that sequences are identical over a window of comparison. Sequence identity may be determined by alignment of compared sequences using computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The disclosure also provides derivatives of anti-IL-3Rα immunoglobulins, antibodies or antigen binding fragments of the disclosure. As used herein, "derivative" proteins have been altered, for example by post-translational modification (e.g. phosphorylation, acetylation etc), modification of glycosylation (e.g. adding, removing or altering glycosylation) and/or inclusion of additional amino acid sequences as would be understood in the art.

The term "nucleic acid" as used herein designates single- or double-stranded DNA and RNA capable of encoding an immunoglobulin, antibody or antigen binding fragment of the disclosure or a polypeptide component thereof. DNA includes genomic DNA and cDNA. RNA includes mRNA and cRNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

"Hybridize and Hybridization" is used herein to denote the pairing of at least partly complementary nucleotide sequences to produce a DNA-DNA, RNA-RNA or DNA-RNA hybrid. Hybrid sequences comprising complementary nucleotide sequences occur through base-pairing between complementary purines and pyrimidines as are well known in the art.

In this regard, it will be appreciated that modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"High stringency conditions" designates those conditions under which only nucleic acid having a high frequency of complementary bases will hybridize.

Reference herein to high stringency conditions include and encompass:—
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and
(iii) 0.2×SSC, 0.1% SDS for washing at or above 68° C. for about 20 minutes.

In general, washing is carried out at $T_m=69.3+0.41$ (G+C) %−12° C. In general, the $T_m$ of a duplex DNA decreases by about 1° C. with every increase of 1% in the number of mismatched bases.

Notwithstanding the above, stringent conditions are known in the art, such as described in Chapters 2.9 and 2.10 of. Ausubel et al., CURRENT PROTOCOLS IN MOLECULAR BIOLOGY John Wiley & Sons, Inc. 1995-2009

An "expression vector" may be either a self-replicating extra-chromosomal vector such as a plasmid, or a vector that integrates into a host genome.

Immunoglobulins

Suitably, an immunoglobulin or antibody of the disclosure selectively binds IL-3Rα chain, by which is meant that the binding interaction between the immunoglobulin or antibody and IL-3Rα chain is dependent on the presence of the antigenic determinant or epitope of an IL-3Rα chain bound by the immunoglobulin. Accordingly, the immunoglobulin or antibody preferentially binds or recognizes an IL-3Rα chain antigenic determinant or epitope even when present in a mixture of other molecules or organisms.

Antibodies

In one example, an immunoglobulin as described herein according to any example is an antibody, e.g., comprising CDRs and/or one or more variable regions described herein.

Suitably, the immunoglobulin is a humanized, chimeric or human antibody that comprises light and heavy chain CDR 1, 2 and 3 amino acid sequences according to SEQ ID NOs: 2-7 respectively. In one example, the antibody comprise a heavy chain variable region amino acid sequence according to SEQ ID NO: 9 and a light chain variable region amino acid sequence according to SEQ ID NO: 8. In one example, the antibody comprises a heavy chain amino acid sequence according to SEQ ID NO: 10, SEQ ID NO: 11 or SEQ ID NO: 12 and a light chain amino acid sequence according to SEQ ID NO: 13.

In one example, the antibody is a recombinant antibody. Methods for producing antibodies comprising CDRs and/or variable regions described herein will be apparent to the skilled artisan based on the disclosure herein and/or documents referred to herein.

In one example, an antibody of the disclosure comprises a $V_H$ and/or a $V_L$, comprising CDRs as set forth herein and FRs from a human antibody. Optionally, the FRs comprise one or more amino acid substitutions, e.g., 2 or more or 3 or more or 4 or more of 5 or more or 10 or more or 15 or more. In one example, the FRs comprise no more than 30 amino acid substitutions, e.g., no more than 20 amino acid substitutions compared to the human FRs.

In one example, an antibody of the disclosure comprises a $V_H$ and/or a $V_L$ comprising CDRs as set forth herein and FRs from a non-human primate antibody, i.e., the antibody is Synhumanized, e.g., as described in WO2007/019620.

In one example, an antibody of the disclosure is a composite antibody, e.g., as described in WO2006/082406.

One exemplary antibody of the disclosure is a humanized antibody, e.g., as defined herein. Exemplary humanized antibodies are described herein. In one example, the humanized antibody has been affinity matured. In one example, the humanized antibody comprises:

(i) a $V_L$ comprising:
  a) a CDR1 comprising a sequence set forth in SEQ ID NO: 2 (or encoded by a sequence set forth in SEQ ID NO: 14);
  b) a CDR2 comprising a sequence set forth in SEQ ID NO: 3 (or encoded by a sequence set forth in SEQ ID NO: 15); and
  c) a CDR3 comprising a sequence set forth in SEQ ID NO: 4 (or encoded by a sequence set forth in SEQ ID NO: 16); and (ii) a $V_H$ comprising:
  d) a CDR1 comprising a sequence set forth in SEQ ID NO: 5 (or encoded by a sequence set forth in SEQ ID NO: 17);
  e) a CDR2 comprising a sequence set forth in SEQ ID NO: 6 (or encoded by a sequence set forth in SEQ ID NO: 18); and
  f) a CDR3 comprising a sequence set forth in SEQ ID NO: 7 (or encoded by a sequence set forth in SEQ ID NO: 19).

Those skilled in the art will appreciate that immunoglobulins or antibodies of the disclosure may include modifications that introduce sequences not naturally found in humans, for example to increase affinity or effector function.

The disclosure also provides variants of the immunoglobulin or antibody of the disclosure. Suitably, variants have at least 80%, 85%, 90%, 91%, 92%, 93%, 94%, 95%, 96%, 97%, 98% or 99% sequence identity with any of the amino acid sequences set forth in SEQ ID NOS:2-13.

For example, it is understood in the art that some amino acids may be substituted or deleted without adversely or significantly affecting the IL-3Rα specificity and/or effector function of the immunoglobulin or antibody (e.g. conservative substitutions).

Derivatives of antibodies or immunoglobulins contemplated by the disclosure include, but are not limited to, modification to amino acid side chains, incorporation of unnatural amino acids and/or their derivatives during peptide or polypeptide synthesis and the use of crosslinkers.

Exemplary antibodies and antigen binding fragments thereof of the present disclosure are described in Table 1.

TABLE 1

Exemplary antibodies and antigen binding fragments thereof

| Name | Heavy Chain SEQ ID NO: | Light Chain SEQ ID NO: |
|---|---|---|
| CSL362 Fv | 9[1] | 8[1] |
| CSL362 | 10 | 13 |
| CSL362B | 10[2] | 13 |
| CSL362X1 | 11 | 13 |
| CSL362X2 | 12 | 13 |

[1]Variable region sequence only.
[2]Heavy chain constant region is afucosylated.

Antibody Fragments
Single-Domain Antibodies

In some examples, an antigen binding fragment of an antibody of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Diabodies, Triabodies, Tetrabodies

In some examples, an antigen binding fragment of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

A diabody, triabody, tetrabody, etc capable of inducing effector activity can be produced using an antigen binding domain capable of binding to IL-3Rα and an antigen binding domain capable of binding to a cell surface molecule on an immune cell, e.g., a T cell (e.g., CD3).

Single Chain Fv (scFv) Fragments

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

The present disclosure also contemplates a dimeric scFv capable of inducing effector activity. For example, one scFv binds to IL-3Rα and comprises CDRs and/or variable regions described herein and another scFv binds to a cell surface molecule on an immune cell, e.g., a T cell (e.g., CD3 or CD19). In one example, the dimeric protein is a combination of a dAb and a scFv. Examples of bispecific antibody fragments capable of inducing effector function are described, for example, in U.S. Pat. No. 7,235,641.

Other Antibodies and Antibody Fragments

The present disclosure also contemplates other antibodies and antibody fragments, such as:

(i) "key and hole" bispecific proteins as described in U.S. Pat. No. 5,731,168;
(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) Fab$_3$ (e.g., as described in EP19930302894).

Constant Regions

The present disclosure encompasses immunoglobulins and antibodies and antigen binding fragments comprising a constant region of an antibody and/or a Fc region of an antibody.

Sequences of constant regions and/or Fc regions useful for producing the immunoglobulins, antibodies or antigen binding fragments of the present disclosure may be obtained from a number of different sources. In some examples, the constant region, Fc or portion thereof of the immunoglobulin, antibody or antigen binding fragment is derived from a human antibody. The constant region, Fc or portion thereof may be derived from any antibody class, including IgA, IgM, IgG, IgD, IgA and IgE, and any antibody isotype, including IgG1, IgG2, IgG3 and IgG4. In one example, the constant region or Fc is human isotype IgG1 or human isotype IgG2 or human isotype IgG3 or a hybrid of any of the foregoing.

In one example, the constant region or Fc region is capable of inducing an effector function. For example, the constant region or Fc region is a human IgG1 or IgG3 Fc region. In another example, the constant region or Fc region is a hybrid of an IgG1 and an IgG2 constant region or Fc region or a hybrid of an IgG1 and an IgG3 constant region or Fc region or a hybrid of an IgG2 and an IgG3 constant region or Fc region. Exemplary hybrids of human IgG1 and IgG2 constant region or Fc regions are described in Chappel et al., *Proc. Natl. Acad. Sci. USA*, 88: 9036-9040, 1991.

Methods for determining whether or not a Fc region can induce effector function will be apparent to the skilled artisan and/or described herein.

Effector Function

Suitably, an anti-IL-3Rα immunoglobulin, antibody or antigen binding fragment of the disclosure has or displays an effector function that facilitates or enables at least partial depletion, substantial depletion or elimination of IL-3Rα$^+$ cells. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

As will be apparent to the skilled artisan based on the description herein, some examples of the present disclosure include an immunoglobulin, antibody or antigen binding fragment capable of inducing effector function.

For the IgG class of antibodies, these effector functions are governed by engagement of the Fc region with a family of receptors referred to as the Fcγ receptors (FcγRs) which are expressed on a variety of immune cells and/or with complement, e.g., C1q. Formation of the Fc/FcγR complex recruits these cells to sites of bound antigen, typically resulting in signaling and subsequent immune responses. Methods for optimizing the binding affinity of the FcγRs to the antibody Fc region in order to enhance the effector functions, in particular to alter the ADCC and/or CDC activity relative to the "parent" Fc region, are known to persons skilled in the art. These methods can include modification of the Fc region of the antibody to enhance its interaction with relevant Fc receptors and increase its potential to facilitate ADCC and ADCP. Enhancements in ADCC activity have also been described following the modification of the oligosaccharide covalently attached to IgG1 antibodies at the conserved Asn297 in the Fc region.

In this regard, it will be appreciated that in some non-limiting examples, enhancing effector function such as ADCC may be achieved by modification of an immunoglobulin or antibody which has a normally glycosylated wild-type constant domain, including alteration or removal of glycosylation (see for example WO00/61739) and/or amino acid sequence mutations (see for example WO2008036688).

In one example, the immunoglobulin, antibody or antigen binding fragment binds to IL-3Rα in such a manner that it is capable of inducing an effector function, such as, ADCC.

In one example, the immunoglobulin, antibody or antigen binding fragment binds to an epitope within IL-3Rα that permits it to induce an effector function, such as ADCC.

In another example, the immunoglobulin, antibody or antigen binding fragment is capable of binding to IL-3Rα on a cell in a mammal to thereby induce an effector function, such as ADCC.

For example, the immunoglobulin, antibody or antigen binding fragment remains bound to IL-3Rα on the surface of a cell for a time sufficient to induce an effector function, such as ADCC. For example, the immunoglobulin or antibody is not internalized too quickly to permit ADCC to be induced.

Alternatively, or in addition, the immunoglobulin, antibody or antigen binding fragment is bound to the IL-3Rα on the surface of the cell in a manner permitting an immune effector cell to bind to a constant region or Fc region in the immunoglobulin, antibody or antigen binding fragment and induce an effector function, such as ADCC. For example, the Fc region of the immunoglobulin, antibody or antigen binding fragment is exposed in such a manner when the immunoglobulin, antibody or antigen binding fragment is bound to the IL-3Rα that is capable of interacting with a Fc receptor (e.g., a FcγR) on an immune effector cell. In the context of the present disclosure, the term "immune effector cell" shall be understood to mean any cell that expresses a Fc receptor and that is capable of killing a cell to which it is bound by ADCC or ADCP. In one example, the immune effector cell is a NK cell.

Each of the above paragraphs relating to effector functions of an immunoglobulin, antibody or antigen binding fragment shall be taken to apply mutatis mutandis to inducing CDC. For example, the immunoglobulin, antibody or antigen binding fragment is bound to the IL-3Rα on the surface of the cell in a manner permitting complement component C1q to bind to a constant region or Fc region in the immunoglobulin, antibody or antigen binding fragment and induce CDC.

In one example, the immunoglobulin, antibody or antigen binding fragment is capable of inducing an enhanced level of effector function.

In one example, the level of effector function induced by the constant region or Fc region is enhanced relative to a wild-type constant region or Fc region of an IgG1 antibody or a wild-type constant region or Fc region of an IgG3 antibody.

In another example, the constant region or Fc region is modified to increase the level of effector function it is capable of inducing compared to the constant region or Fc region without the modification. Such modifications can be at the amino acid level and/or the secondary structural level and/or the tertiary structural level and/or to the glycosylation of the constant region or Fc region.

The skilled addressee will appreciate that greater effector function may be manifested in any of a number of ways, for example as a greater level of effect, a more sustained effect or a faster rate of effect.

For example, the anti-IL-3Rα immunoglobulin, antibody or antigen binding fragment has or displays an effector function that includes antibody-dependent cell-mediated cytotoxicity (ADCC).

In one example, the constant region or Fc region comprises one or more amino acid modifications that increase its ability to induce enhanced effector function. In one example, the constant region or Fc region binds with greater affinity to one or more FcγRs. In one example, the constant region or Fc region has an affinity for an FcγR that is more than 1-fold greater than that of a wild-type constant region or Fc region or more than 5-fold greater than that of a wild-type constant region or Fc region or between 5-fold and 300-fold greater than that of a wild-type constant region or Fc region. In one example, the constant region or Fc region comprises at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the constant region or Fc region comprise at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the constant region or Fc region comprises amino acid substitutions selected from the group consisting of V264I, F243LN2641, L328M, I332E, L328M/I332E, V264I/ I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E-V264I/ I332E, S239Q/V264I/I332E, S239E/V264I/A330Y/I332E, S239D/A330Y/I332E, S239N/A330Y/I332E, S239D/ A330L/I332E, S239N/A330L/I332E, V264I/S298A/I332E, S239D/S298A/I332E, S239N/S298A/I332E, S239D/V264I/ I332E, S239D/V264I/S298A/I332E, S239D/V2641/A330L/ I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V2661, S239D/A330Y/I332E/L234I, S239D/A330Y/I332E/ L235D, S239D/A330Y/I332E/V2401, S239D/A330Y/ I332EN264T, S239D/A330Y/I332E/K326E, and S239D/ A330Y/I332E/K326T, numbered according to the EU index of Kabat.

In another example, the constant region or Fc region binds to FcγRIIIa more efficiently than to FcγRIIb. For example, the constant region or Fc region comprises at least one amino acid substitution at a position selected from the group consisting of: 234, 235, 239, 240, 264, 296, 330, and I332, numbered according to the EU index of Kabat. In one example, the constant region or Fc region comprises at least one amino acid substitution selected from the group consisting of: L234Y, L234I, L235I, S239D, S239E, S239N, S239Q, V240A, V240M, V264I, V264Y, Y296Q, A330L, A330Y, A330I, I332D, and I332E, numbered according to the EU index of Kabat. For example, the constant region or Fc region comprises amino acid substitutions selected from the group consisting of: I332E, V264I/I332E, S239E/I332E, S239Q/ I332E, Y296Q, A330L, A330Y, I332D, S239D, S239D/ I332E, A330Y/I332E, V264I/A330Y/I332E, A330L/I332E, V264I/A330L/I332E, L234Y, L234I, L235I, V240A, V240M, V264Y, A330I, S239D/A330L/I332E, S239D/ S298A/I332E, S239N/S298A/I332E, S239D/V264I/I332E, S239D/V264I/S298A/I332E, and S239D/V264I/A330L/ I332E, numbered according to the EU index of Kabat.

In a further example, the constant region or Fc region induces ADCC at a level greater than that mediated by a wild-type constant region or Fc region. For example, the constant region or Fc region induces ADCC at a level that is more than 5-fold or between 5-fold and 1000-fold greater than that induced by a wild-type constant region or Fc region. In one example, the constant region or Fc region comprises at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the constant region or Fc region comprises at least one amino acid substitutions selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the constant region or Fc region comprises amino acid substitutions selected from the group consisting of: V264I, F243LN2641, L328M, I332E, L328M/I332E, V264I/ I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/ I332E, S239Q/V264I/I332E, S239E/V264I/A330Y/I332E, S239D/A330Y/I332E, S239N/A330Y/I332E, S239D/ A330L/I332E, S239N/A330L/I332E, V264I/S298A/I332E, S239D/S298A/I332E, S239N/S298A/I332E, S239D/V264I/ I332E, S239D/V264I/S298A/I332E, S239D/V264I/A330L/ I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V2661, S239D/A330Y/I332E/L234I, S239D/A330Y/I332E/L235D, S239D/A330Y/I332EN240I, S239D/A330Y/I332EN264T, S239D/A330Y/I332E/K326E, and S239D/A330Y/I332E/ K326T, numbered according to the EU index of Kabat.

In one example, the constant region or Fc region comprises the following amino acid substitutions S239D/I332E, numbered according to the EU index of Kabat. This constant region or Fc region has about 14 fold increase in affinity for FcγRIIIa compared to a wild-type constant region or Fc region and about 3.3 increased ability to induce ADCC compared to a wild-type constant region or Fc region. In one example, the constant region comprises a sequence set forth between residues 121-450 (inclusive) of SEQ ID NO: 11. In one example, the Fc region comprises a sequence set forth between residues 234-450 of SEQ ID NO: 11.

In one example, the constant region or Fc region comprises the following amino acid substitutions S239D/A330L/I332E, numbered according to the EU index of Kabat. This constant region or Fc region has about 138 fold increase in affinity for FcγRIIIa compared to a wild-type constant region or Fc region and about 323 increased ability to induce ADCC compared to a wild-type constant region or Fc region. In one example, the constant region comprises a sequence set forth between residues 121-450 (inclusive) of SEQ ID NO: 12. In one example, the Fc region comprises a sequence set forth between residues 234-450 of SEQ ID NO: 12.

Additional amino acid substitutions that increase ability of a Fc region to induce effector function are known in the art and/or described, for example, in U.S. Pat. No. 6,737,056 or U.S. Pat. No. 7,317,091.

In one example, the glycosylation of the constant region or Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the constant region or Fc region. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some examples, constant regions or Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the immunoglobulin or antibody in a cell line incapable of expressing α-1,6-fucosyltransferase (FUT8) (e.g., as described in Yumane-Ohnuki et al., *Biotechnol. Bioengineer.*, 87: 614-622, 2004), expressing the immunoglobulin or antibody in cells expressing a small interfering RNA against FUT8 (e.g., as described in Mori et al., *Biotechnol. Bioengineer.*, 88: 901-908, 2004), expressing the immunoglobulin or antibody in cells incapable of expressing guanosine diphosphate (GDP)-mannose 4,6-dehydratase (GMD) (e.g., as described in Kanda et al., *J. Biotechnol.*, 130: 300-310, 2007). The present disclosure also contemplates the use of immunoglobulins having a reduced level of fucosylation, e.g., produced using a cell line modified to express β-(1,4)-N-acetyl-glucosaminyltransferase III (GnT-III) (e.g., as described in Umana et al., *Nat. Biotechnol.*, 17: 176-180, 1999).

In one example, an immunoglobulin or antibody according to the present disclosure is afucosylated. For example, the immunoglobulin or antibody is produced in a cell (e.g., a mammalian cell, such as a CHO cell) that does not express FUT8.

Other methods include the use of cell lines which inherently produce antibodies capable of inducing enhanced Fc-mediated effector function (e.g. duck embryonic derived stem cells for the production of viral vaccines, WO2008/129058; Recombinant protein production in avian EBX® cells, WO 2008/142124).

Immunoglobulins useful in the methods of the present disclosure also include those with bisected oligosaccharides, e.g., in which a biantennary oligosaccharide attached to the constant region or Fc region is bisected by GlcNAc. Such immunoglobulins may have reduced fucosylation and/or improved ADCC function. Examples of such immunoglobulins are described, e.g., in U.S. Pat. No. 6,602,684 and US20050123546.

Immunoglobulins with at least one galactose residue in the oligosaccharide attached to the constant region or Fc region are also contemplated. Such immunoglobulins may have improved CDC function. Such immunoglobulins are described, e.g., in WO1997/30087 and WO1999/22764.

Non-limiting examples of immunoglobulins that induce enhanced levels of ADCC activity include:

(i) an antibody comprising a heavy chain comprising a sequence set forth in SEQ ID NO: 11 and a light chain comprising a sequence set forth in SEQ ID NO: 13;

(ii) an antibody comprising a heavy chain comprising a sequence set forth in SEQ ID NO: 12 and a light chain comprising a sequence set forth in SEQ ID NO: 13; and (iii) an antibody comprising a heavy chain comprising a sequence set forth in SEQ ID NO: 10 and a light chain comprising a sequence set forth in SEQ ID NO: 13, wherein the heavy chain constant region is afucosylated.

An advantageous antibody of the disclosure that induces enhanced levels of ADCC activity comprises a heavy chain comprising a sequence set forth in SEQ ID NO: 11 and a light chain comprising a sequence set forth in SEQ ID NO: 13. As discussed herein, after administering this antibody to a mammal (e.g., at least 7 or 8 or 11 or 17 or 22 or 29 days after administration) the number of NK cells in a mammal is increased compared to one or more of:

(i) the number of NK cells in the mammal prior art administration of the antibody;

(ii) the number of NK cells in a mammal administered an antibody comprising a heavy chain comprising a sequence set forth in SEQ ID NO: 10 and a light chain comprising a sequence set forth in SEQ ID NO: 13, wherein the heavy chain constant region is afucosylated (e.g., as assessed on the same day after administration); and (iii) the number of NK cells in a mammal administered an antibody that binds specifically to IL-3Rα chain and has a human IgG1 constant region (e.g., as assessed on the same day after administration).

Methods for determining the ability of an immunoglobulin or antibody to induce effector function and known in the art and/or described in more detail herein.

Additional Modifications

The present disclosure also contemplates additional modifications to an immunoglobulin.

For example, the immunoglobulin or antibody comprises one or more amino acid substitutions that increase the half-life of the immunoglobulin. For example, the immunoglobulin or antibody comprises a constant region or Fc region comprising one or more amino acid substitutions that increase the affinity of the constant region or Fc region for the neonatal Fc region (FcRn). For example, the constant region or Fc region has increased affinity for FcRn at lower pH, e.g., about pH 6.0, to facilitate Fc/FcRn binding in an endosome. In one example, the constant region or Fc region has increased affinity for FcRn at about pH 6 compared to its affinity at about pH 7.4, which facilitates the re-release of constant region or Fc into blood following cellular recycling. These amino acid substitutions are useful for extending the half life of an immunoglobulin, by reducing clearance from the blood.

Exemplary amino acid substitutions include T250Q and/or M428L according to the EU numbering system of Kabat. Additional or alternative amino acid substitutions are described, for example, in US20070135620.

Nucleic Acids

Another example of the disclosure provides an isolated nucleic acid that encodes an immunoglobulin or antibody of the disclosure, inclusive of fragments, variants and derivatives of the immunoglobulin or antibody.

Certain examples of nucleic acids comprise a nucleotide sequence set forth in one or more of SEQ ID NOS:14-19, which respectively encode CDRs1-6 of an immunoglobulin or antibody of the disclosure.

Other examples of nucleic acids comprise a nucleotide sequence set forth in one or more of SEQ ID NOS: 20-23.

The disclosure also contemplates nucleic acid homologs that encode a variant of an immunoglobulin or antibody of the disclosure, as hereinbefore described.

Exemplary, nucleic acid homologs share at least 80% or 85%, such as at least 90% or 95% or 99% nucleotide sequence identity with an isolated nucleic acid that encodes any one of SEQ ID NOS:2-13. Suitably, the nucleic acid homolog does not encode a protein comprising a murine variable region capable of binding specifically to IL-3Rα.

Nucleic acid homologs may hybridize to isolated nucleic acids of the disclosure under high stringency conditions.

Protein Production

Recombinant Expression

In one example, an immunoglobulin or antibody described herein according to any example is recombinant.

By way of example only, a recombinant immunoglobulin or antibody of the disclosure may be produced by a method including the steps of:
  (i) preparing an expression construct which comprises an isolated nucleic acid of disclosure, operably linked to one or more regulatory nucleotide sequences (e.g., a promoter);
  (ii) transfecting or transforming a suitable host cell with the expression construct;
  (iii) expressing a recombinant immunoglobulin or antibody in the host cell; and
  (iv) isolating the recombinant immunoglobulin or antibody from the host cell.

In the case of a recombinant immunoglobulin, nucleic acid encoding same can be cloned into expression vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin or antibody protein.

Exemplary cells used for expressing an immunoglobulin or antibody are CHO cells, myeloma cells or HEK cells. The cell may further comprise one or more genetic mutations and/or deletions that facilitate expression of a modified immunoglobulin or antibody. One non-limiting example is a deletion of a gene encoding an enzyme required for fucosylation of an expressed immunoglobulin or antibody. For example, the deleted gene encodes FUT8. A commercially available source of FUT8-deleted CHO cells is Biowa (Potelligent™ cells). For example, the cells used for expression of an afucosylated immunoglobulin or antibody are FUT8-deleted CHO cells, such as, Biowa's Potelligent™ cells.

Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or U.S. Pat. No. 5,530,101.

Following isolation, the nucleic acid is inserted operably linked to a promoter in an genetic construct or expression vector for further cloning (amplification of the DNA) or for expression in a cell-free system or in cells. Thus, another example of the disclosure provides a genetic construct that comprises an isolated nucleic acid of the disclosure and one or more additional nucleotide sequences. Suitably, the genetic construct is in the form of, or comprises genetic components of, a plasmid, bacteriophage, a cosmid, a yeast or bacterial artificial chromosome as are well understood in the art. Genetic constructs may be suitable for maintenance and propagation of the isolated nucleic acid in bacteria or other host cells, for manipulation by recombinant DNA technology and/or for expression of the nucleic acid or an encoded immunoglobulin or antibody of the disclosure. For the purposes of host cell expression, the genetic construct is an expression construct. Suitably, the expression construct comprises the nucleic acid of the disclosure operably linked to one or more additional sequences in an expression vector, such as a promoter or a regulatory sequence.

Typically, a regulatory nucleotide sequence may include, but are not limited to, promoter sequences, leader or signal sequences, ribosomal binding sites, transcriptional start and termination sequences, translational start and termination sequences, and enhancer or activator sequences.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an immunoglobulin or antibody (e.g., derived from the information provided herein), an enhancer element, a promoter, and a transcription termination sequence. The skilled artisan will be aware of suitable sequences for expression of an immunoglobulin. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin or antibody promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S.*

*pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the immunoglobulin or antibody may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for purifying an immunoglobulin or antibody are known in the art and/or described herein.

Where an immunoglobulin or antibody is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The immunoglobulin or antibody prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbour Laboratory, (1988).

The skilled artisan will also be aware that an immunoglobulin or antibody can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting immunoglobulin or antibody is then purified using methods known in the art, such as, affinity purification. For example, an immunoglobulin or antibody comprising a hexa-his tag is purified by contacting a sample comprising the immunoglobulin or antibody with nickel-nitrilotriacetic acid (Ni-NTA) that specifically binds a hexa-his tag immobilized on a solid or semi-solid support, washing the sample to remove unbound immunoglobulin, and subsequently eluting the bound immunoglobulin. Alternatively, or in addition a ligand or antibody that binds to a tag is used in an affinity purification method.

In one example, the immunoglobulin or antibody also has a protease cleavage site, such as for Factor $X_a$ or Thrombin, which allow the relevant protease to partially digest the immunoglobulin or antibody and thereby liberate the immunoglobulin or antibody from the tag. The liberated antibody or immunoglobulin can then be isolated from the fusion partner by subsequent chromatographic separation.

Assaying Activity of an Immunoglobulin

Immunoglobulins or antibodies of the disclosure are readily screened for biological activity, e.g., as described below.

Binding Assays

One form of such an assay is an antigen binding assay, e.g., as described in Scopes (In: Protein purification: principles and practice, Third Edition, Springer Verlag, 1994). Such a method generally involves labeling the immunoglobulin or antibody and contacting it with immobilized antigen. Following washing to remove non-specific bound protein, the amount of label and, as a consequence, bound protein is detected. Of course, the immunoglobulin or antibody can be immobilized and the antigen labeled. Panning-type assays, e.g., as described or exemplified herein can also be used.

Determining Neutralization

In some examples of the present disclosure, an immunoglobulin or antibody is capable of neutralizing IL-3 signaling.

Various assays are known in the art for assessing the ability of an immunoglobulin to neutralize signaling of a ligand through a receptor.

In one example, the immunoglobulin or antibody reduces or prevents IL-3 binding to the 3Rα chain and/or a heterodimer of IL-3Rα chain and IL-3Rβ chain. These assays can be performed as a competitive binding assay using labeled IL-3 and/or labeled immunoglobulin. For example, labeled IL-3Rα or an extracellular region thereof fused to an Fc region of an antibody or a cell expressing IL-3R immobilized and labeled IL-3 is then contacted to the immobilized receptor or cell in the presence or absence of a test immunoglobulin or antibody and the amount of bound label detected. A reduction in the amount of bound label in the presence of the antibody or immunoglobulin compared to in the absence of the protein indicates that the immunoglobulin or antibody reduces or prevents binding of IL-3 to IL-3R. By testing multiple concentrations of the immunoglobulin or antibody an $IC_{50}$ is determined, i.e., a concentration of the protein that reduces the amount of IL-3 that binds to IL-3R, or an $EC_{50}$ can be determined, i.e., a concentration of the protein that achieves 50% of the maximum inhibition of binding of IL-3 to IL-3R achieved by the immunoglobulin or antibody In another example, the immunoglobulin or antibody reduces or prevents IL-3-mediated histamine release from basophils. For example, low density leukocytes comprising basophils are incubated with IgE, IL-3 and various concentrations of the immunoglobulin or antibody. Control cells do not comprise immunoglobulin (positive control) or IL-3 (negative control). The level of released histamine is then assessed using a standard technique, e.g., RIA. An immunoglobulin or antibody that reduces the level of histamine release to a level less than the positive control is considered to neutralize IL-3 signaling. In one example, the level of reduction is correlated with immunoglobulin or antibody concentration. An exemplary method for assessing IL-3-mediated histamine release is described, for example, in Lopez et al., *J. Cell. Physiol.*, 145: 69, 1990.

In a further example, the immunoglobulin or antibody reduces or prevents IL-3-mediated proliferation of leukemic cell line TF-1. For example, TF-1 cells are cultured without IL-3 or GM-CSF for a time sufficient for them to stop proliferating (e.g., 24-48 hours). Cells are then cultured in the presence of IL-3 and various concentrations of the immunoglobulin or antibody. Control cells are not contacted with the immunoglobulin or antibody (positive control) or IL-3 (negative control). Cell proliferation is then assessed using a standard technique, e.g., $^3$H-thymidine incorporation. An immunoglobulin or antibody that reduces or prevents cell proliferation in the presence of IL-3 to a level less than the positive control is considered to neutralize IL-3 signaling.

Another assay for assessing IL-3 signaling neutralization comprises determining whether or not the immunoglobulin or antibody reduces or prevents IL-3-mediated effects on endothelial cells. For example, human umbilical vein endothelial cells (HUVECs) are cultured in the presence of IL-3 (optionally, with IFN-γ) and various concentrations of the immunoglobulin or antibody. The amount of secreted IL-6 is then assessed, e.g., using an enzyme linked immunosorbent assay (ELISA). Control cultures do not comprise immunoglobulin or antibody (positive control) or IL-3 (negative control). An immunoglobulin or antibody that reduces or prevents IL-6 production in the presence of IL-3 to a level less than the positive control is considered to neutralize IL-3 signaling.

Other methods for assessing neutralization of IL-3 signaling are contemplated by the present disclosure.

Determining Effector Function

Methods for assessing ADCC activity are known in the art.

In one example, the level of ADCC activity is assessed using a $^{51}$Cr release assay, a europium release assay or a $^{35}$S release assay. In each of these assays, cells expressing IL-3Rα are cultured with one or more of the recited compounds for a time and under conditions sufficient for the compound to be taken up by the cell. In the case of a $^{35}$S release assay, cells expressing IL-3Rα can be cultured with $^{35}$S-labeled methionine and/or cysteine for a time sufficient for the labeled amino acids to be incorporated into newly synthesized proteins. Cells are then cultured in the presence or absence of the immunoglobulin or antibody and in the presence of immune effector cells, e.g., peripheral blood mononuclear cells (PBMC) and/or NK cells. The amount of $^{51}$Cr, europium and/or $^{35}$S in cell culture medium is then detected, and an increase in the presence of the immunoglobulin or antibody compared to in the absence of immunoglobulin indicates that the immunoglobulin has effector function. Exemplary publications disclosing assays for assessing the level of ADCC induced by an immunoglobulin include Hellstrom, et al. *Proc. Natl. Acad. Sci. USA* 83:7059-7063, 1986 and Bruggemann, et al., *J. Exp. Med.* 166:1351-1361, 1987.

Other assays for assessing the level of ADCC induced by an immunoglobulin or antibody include ACTI™ nonradioactive cytotoxicity assay for flow cytometry (CellTechnology, Inc. CA, USA) or CytoTox 96® non-radioactive cytotoxicity assay (Promega, Wis., USA).

Alternatively, or additionally, effector function of an immunoglobulin or antibody is assessed by determining its affinity for one or more FcγRs, e.g., as described in U.S. Pat. No. 7,317,091.

C1q binding assays may also be carried out to confirm that the immunoglobulin or antibody is able to bind C1q and may induce CDC. To assess complement activation, a CDC assay may be performed (see, for example, Gazzano-Santoro et al, *J. Immunol. Methods* 202: 163, 1996.

Determining NK cell Numbers

As discussed herein, immunoglobulins and/or antibodies of the disclosure can affect the number of NK cells in a mammal. Methods for assessing the number of NK cells in a mammal will be apparent to the skilled artisan.

In one example, following administration of an immunoglobulin or antibody of the disclosure to a mammal (e.g., a non-human mammal, such as a non-human primate, e.g., a cynomolgus monkey) a sample of blood (or serum) is obtained and the number of NK cells assessed using fluorescence activated cell sorting (FACS). NK cells can be detected based on expression of CD16 and/or CD56 and/or lack of expression (or low levels of expression) of CD20 and/or CD3. The percentage change in the number of NK cells can be determined by comparing to the number of NK cells in a sample obtained earlier (e.g., prior to administration of the antibody or immunoglobulin).

Determining Affinity

Optionally, the dissociation constant (Kd) or association constant (Ka) or equilibrium constant ($K_D$) of a protein for IL-3Rα or an epitope thereof is determined. These constants for an immunoglobulin or antibody is, in one example, measured by a radiolabeled or fluorescently-labeled IL-3Rα-binding assay. This assay equilibrates the protein with a minimal concentration of labeled IL-3Rα (or a soluble form thereof, e.g., comprising an extracellular region of IL-3Rα fused to an Fc region) in the presence of a titration series of unlabeled IL-3Rα. Following washing to remove unbound IL-3Rα, the amount of label is determined.

Affinity measurements can be determined by standard methodology for antibody reactions, for example, immunoassays, surface plasmon resonance (SPR) (Rich and Myszka *Curr. Opin. Biotechnol* 11::54, 2000; Englebienne *Analyst.* 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized IL-3Rα or a region thereof. Exemplary SPR methods are described in U.S. Pat. No. 7,229,619.

Assessing Therapeutic Efficacy

In Vitro Assays

Various in vitro assays are available to assess the ability of an immunoglobulin or antibody to treat a disease or condition described herein.

For example, an immunoglobulin or antibody is assessed for its ability to kill a cell, e.g., a cancer cell, such as leukemic cell, using a method described herein.

In another example, immune cells, e.g., pDCs and/or basophils or cell populations comprising same (e.g., PBMC) are cultured in the presence or absence of an immunoglobulin or antibody and an inducer of those cells that occurs in a disease or condition (e.g., CpG oligonucleotides and/or immune complexes). The efficacy of the immunoglobulin or antibody in treating the disease or condition is then assessed, e.g., by determining the level of IFNα secreted into cell culture medium using an ELISA. Alternatively or in addition the level of histamine secretion or IL-4, IL-6 and/or IL-13 secretion is assessed. A reduction in the level of any of these cytokines compared to in the absence of immunoglobulin or antibody (or in the presence of an isotype control immunoglobulin or antibody) indicates that the immunoglobulin or antibody is suitable for treating the disease or condition. Alternatively, or in addition, the level of cell death is assessed. An increase in cell death is indicative of an immunoglobulin or antibody suitable for treating the disease or condition.

In Vivo Assays

In one example, the efficacy of an immunoglobulin to treat a disease or condition is assessed using an in vivo assay.

In one example, a xenotransplantation model of a cancer is used to assess therapeutic efficacy. For example, NOD/SCID mice are irradiated and optionally treated with anti-CD122 antibody to deplete NK cells. Human leukemic cells (e.g., acute myeloid leukemia cells) and mouse or human bone marrow stem cells are administered to the mice. Following cell engraftment, a test immunoglobulin or antibody is administered to the mice and the level of leukemic cells in circulation and/or bone marrow and/or lymph nodes is assessed. A reduction in the number of leukemic cells in circulation and/or bone marrow and/or lymph nodes in the presence of the antibody or immunoglobulin compared to in the absence of the antibody or immunoglobulin indicates therapeutic efficacy.

In another example, the immunoglobulin or antibody is administered to a non-human animal (e.g., a non-human primate) and the number/level of immune cells, e.g., pDCs and/or basophils, in circulation is assessed. An immunoglobulin or antibody that reduces the number/level of immune cells, e.g., pDCs and/or basophils compared to prior to administration and/or in a control mammal to which the immunoglobulin or antibody has not been administered is considered suitable for treating the disease or condition.

In another example, the level of a cytokine, such as IFNα is detected in the circulation of a mammal, e.g., using an ELISA. An immunoglobulin or antibody that reduces the level of the cytokine compared to the level prior to administration and/or in a control mammal to which the immunoglobulin or antibody has not been administered is considered suitable for treating the disease or condition. Since cytokines such as IFNα are considered to play a role in some diseases/conditions, e.g., lupus, an immunoglobulin or antibody that reduces IFNα production is considered to be suitable for treating such conditions.

Compositions

Suitably, in compositions or methods for administration of the anti-IL-3Rα immunoglobulin or antibody to a mammal, the immunoglobulin or antibody is combined with a pharmaceutically acceptable carrier, diluent and/or excipient, as is understood in the art. Accordingly, one example of the present disclosure provides a pharmaceutical composition comprising the immunoglobulin or antibody of the disclosure combined with a pharmaceutically acceptable carrier, diluent and/or excipient. In another example, the disclosure provides a kit comprising a pharmaceutically acceptable carrier, diluent and/or excipient suitable for combining or mixing with the immunoglobulin or antibody prior to administration to the mammal. In this example, the kit may further comprise instructions for use.

In general terms, by "carrier, diluent or excipient" is meant a solid or liquid filler, binder, diluent, encapsulating substance, emulsifier, wetting agent, solvent, suspending agent, coating or lubricant that may be safely administered to any mammal, e.g., a human. Depending upon the particular route of administration, a variety of acceptable carriers, diluents or excipients, known in the art may be used, as for example described in Remington's Pharmaceutical Sciences (Mack Publishing Co. N.J. USA, 1991).

By way of example only, the carriers, diluents or excipients may be selected from a group including sugars (e.g. sucrose, maltose, trehalose, glucose), starches, cellulose and its derivatives, malt, gelatine, talc, calcium sulphate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. For example, the carrier, diluent or excipient is compatible with, or suitable for, parenteral administration. Parenteral administration includes any route of administration that is not through the alimentary canal. Non-limiting examples of parenteral administration include injection, infusion and the like. By way of example, administration by injection includes intravenous, intra-arterial, intramuscular and subcutaneous injection. Also contemplated is delivery by a depot or slow-release formulation which may be delivered intradermally, intramuscularly and subcutaneously, for example.

Combination Therapies

In one example, the immunoglobulin or antibody of the disclosure is administered in combination with another compound or therapeutic treatment useful for treating a disease or condition.

In one example, the immunoglobulin or antibody is administered prior to, e.g., one month or one fortnight or one week prior to radiation therapy, e.g., for the treatment of cancer, such as a hematologic cancer, such as leukemia.

In one example, the other compound is a chemotherapy compound, such as caboplatin, cisplatin, cyclophosphamide, docetaxal, doxorubicin, erlotinib, etoposide, fluorouracil, irinotecan, methotrexate, paclitaxel, topotecan, vincristine or vinblastine. In one example, the chemotherapy compound is selected from the group consisting of methotrexate, 1-asparaginase, vincristine, doxorubicin, danorubicin, cytarabine, idarubicin, mitoxantrone, cyclophosphamide, fludarabine, chlorambucil and combinations thereof.

In one example, the other compound is a chemotherapy compound used in the treatment of acute leukemia, such as, a compound selected from the group consisting of methotrexate, 1-asparaginase, vincristine, doxorubicin, danorubicin, cytarabine, idarubicin, mitoxantrone and combinations thereof.

In one example, the other compound is a chemotherapy compound used in the treatment of acute lymphoblastic leukemia, such as, a compound selected from the group consisting of methotrexate, 1-asparaginase, vincristine, doxorubicin, danorubicin and combinations thereof.

In a further example, the other compound is a chemotherapy compound such as azacytidine.

In one example, the other compound is a biologic useful for treating a cancer, e.g., rituximab, trastuzumab, bevacizumab, alemtuzumab, panitumumab, or cetuximab In one example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is an antimalarial compound, such as hydroxychloroquine or chloroquinine. Alternatively, or additionally, the other compound is methotrexate. Alternatively, or additionally, the other compound is azathioprine. Alternatively, or additionally, the other compound is cyclophosphamide. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab).

Dosages and Timing of Administration

For the prevention or treatment of a disease or condition or relapse thereof, the appropriate dosage of an active agent (i.e., an immunoglobulin or antibody of the disclosure), will depend on the type of disease to be treated, the severity and course of the disease, whether the immunoglobulin or antibody is administered for preventive or therapeutic purposes, previous therapy, the patient's clinical history and response to the immunoglobulin, and the discretion of the attending physician. The particular dosage regimen, i.e., dose, timing, and repetition, will depend on the particular individual and that individual's medical history as assessed by a physician. Typically, a clinician will administer an immunoglobulin until a dosage is reached that achieves the desired result.

Methods of the present disclosure are useful for treating, ameliorating or preventing the symptoms of diseases or conditions in a mammal, or for improving the prognosis of a mammal. Methods of the present disclosure are also useful for delaying development of or preventing lupus in an individual at risk of developing lupus or a relapse thereof.

For administration of the immunoglobulins or antibodies described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, the immunoglobulin or antibody is administered at an initial (or loading) dose of between about 1 mg/kg to about 30 mg/kg, such as from about 1 mg/kg to about 10 mg/kg, or about 2 mg/kg or about 3 mg/kg or 4 mg/kg or 5 mg/kg. The immunoglobulin or antibody can then be administered at a maintenance dose of between about 0.0001 mg/kg to about 1 mg/kg, such as from about 0.0005 mg/kg to about 1 mg/kg, for example, from about 0.001 mg/kg to about 1 mg/kg, such as about 0.01 mg/kg to about 1 mg/kg, for example from about 0.01 mg/kg to about 0.1 mg/kg, such as about 0.02 mg/kg or 0.03 mg/kg or 0.04 mg/kg or 0.05 mg/kg. The maintenance doses may be administered every 7-30 days, such as, every 10-15 days, for example, every 10 or 11 or 12 or 13 or 14 or 15 days.

In some examples, the immunoglobulin or antibody is administered at a dose of between about 0.0001 mg/kg to about 50 mg/kg, such as between about 0.0005 mg/kg to about 50 mg/kg, for example, between about 0.001 mg/kg to about 40 mg/kg, for example, between about 0.005 mg/kg to about 30 mg/kg, such as between about 0.01 mg/kg to about 20 mg/kg. For example, the immunoglobulin is administered at a dose of between about 0.01 mg/kg to about 10 mg/kg, such as from about 0.01 mg/kg to about 1 mg/kg, such as about 0.02 mg/kg or 0.03 mg/kg or 0.04 mg/kg or 0.05 mg/kg or 0.06 mg/kg or 0.07 mg/kg or 0.08 mg/kg or 0.09 mg/kg or 0.1 mg/kg or 0.2 mg/kg or 0.3 mg/kg or 0.4 mg/kg or 0.5 mg/kg or 0.6 mg/kg or 0.7 mg/kg or 0.8 mg/kg or 0.9 mg/kg (e.g., without a higher loading dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the immunoglobulin or antibody is administered every 7 days or every 14 days or every 21 days.

In some examples, the immunoglobulin or antibody is administered at a dose of between about 1 mg/kg to about 30 mg/kg, such as from about 1 mg/kg to about 10 mg/kg, or about 2 mg/kg or about 3 mg/kg or 4 mg/kg or 5 mg/kg, or such as from about 10 mg/kg to 30 mg/kg, such as about 10 mg/kg or 15 mg/kg or 20 mg/kg or 25 mg/kg (e.g., without a lower maintenance dose). In some examples, numerous doses are administered, e.g., every 10-70 days, such as every 14-70 days, such as, every 14-60 days, for example, every 14-50 days, such as every 14-40 days, or every 14-30 days. For example the doses are administered every 14 or 21 or 25 or 28 or 35 or 40 or 42 or 49 or 50 or 55 or 57 or 63 or 70 days. For example, the immunoglobulin or antibody is administered every 21 days or every 28 days or every 35 days or every 42 days or every 49 days or every 56 days.

In some examples, the immunoglobulin or antibody causes or is associated with a reduction of NK cells in a mammal following administration, e.g., within about 6 hours of administration. In some examples, a further dose of the immunoglobulin or antibody is administered when the number of NK cells in a mammal returns to within 20% or 10% or 5% or 1% of the number of NK cells in the mammal prior to administration. In some examples, a further dose of the immunoglobulin or antibody is administered when the number of NK cells in a mammal exceeds the number of NK cells in the mammal prior to administration by at least about 5% or 10% or 20% or 30% or 40% or 50% or 60% or 70% or 80%. The number of NK cells can be assessed in a mammal to determine when to administer the further dose of the immunoglobulin or antibody. Alternatively, the time to administer a further dose of the immunoglobulin or antibody is determined by previous analysis of a population or a model organism (e.g., a non-human primate, such as a cynomolgus monkey). For example, the further dose of the immunoglobulin is administered about 7 days or 8 days or 14 days or 17 days or 21 days or 22 days or 28 days or 29 days following a previous dose.

In some examples, at the time of commencing therapy, the mammal is administered the immunoglobulin or antibody on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Dosages for a particular immunoglobulin or antibody may be determined empirically in mammals that have been given one or more administrations of the immunoglobulin. To assess efficacy of an immunoglobulin, a clinical symptom of a disease or condition can be monitored.

Administration of an immunoglobulin according to the methods of the present disclosure can be continuous or intermittent, depending, for example, on the recipient's physiological condition, whether the purpose of the administration is therapeutic or prophylactic, and other factors known to skilled practitioners. The administration of an immunoglobulin or antibody may be essentially continuous over a preselected period of time or may be in a series of spaced doses, e.g., either during or after development of a condition.

The present disclosure includes the following non-limiting examples.

NON-LIMITING EXAMPLES

Example 1

Humanized Antibodies

A humanized antibody that binds specifically to human IL-3Rα chain that acts as an antagonist of IL-3 activity was produced. The humanized antibody was produced by grafting CDR sequences of an antagonistic murine antibody (7G3) onto human variable framework germline sequences selected on the basis of the canonical structure of the donor and acceptor CDRs in accordance with the procedure of Tan et al., (*J Immunol.* 169, 1119-1125, 2002); sometimes referred to as "superhumanization". This work was conducted using the antibody in a scFv format. This approach then compares the CDR residues of the donor antibody with those of the variable framework germline acceptor sequences, and selects as the acceptor sequence the one with highest correlation of CDR residues. However, in the present case a heavy chain acceptor sequence with a lower level of CDR correlation was selected. The resulting humanized antibody contained entirely human variable framework sequence as a result of the humanization process, however the affinity for IL-3Rα was decreased compared with the parental murine antibody.

Affinity optimization was employed using a ribosome display-based mutagenesis process (Kopsidas et al., *BMC Biotechnol.* 7, 18, 2007) conducted using the antibody in a scFv format in an effort to increase the binding affinity of the humanized antibody. An affinity optimized scFv was produced that when converted to an $IgG_1$ format exhibited slightly improved IL-3Rα binding affinity to that of the parent murine monoclonal antibody. Unpredictably, the affinity optimization process resulted in mutations in the framework of the $V_H$ and $V_L$, as well as in CDR1 of the light chain. So the set of CDR sequences of the humanized affinity optimized antibody differs from those of the parent murine monoclonal antibody. There affinity optimized antibody is referred to herein as CSL362.

Fc engineered derivatives of the humanized affinity optimized antibody comprising the light and heavy chain variable regions of the antibody and a hybrid $IgG_1/IgG2$ constant domain with the three amino acid substitutions S239D/A330L/I332E (referred to herein as CSL362×2) or with the two amino acid substitutions S239D/I332E (referred to herein as CSL362X1) were produced by expression of an appropriate vector in CHO-S cells; the positions of the identified mutations are based on EU numbering system.

An afucosylated version of humanized affinity optimized antibody with a human $IgG_1$ constant domain was generated by expression of an appropriate vector in FUT8-knock-out CHO cells from Biowa (Potelligent® Cells) (referred to herein as CSL362B).

Example 2

Binding Affinity Determination

Full-Length mAb Kinetics:

To analyze full-length antibodies, surface plasmon resonance (Biacore) assays were performed in a capture format where a chemically immobilized anti human or anti mouse Fc specific antibody (Anti human Goat anti Human IgG (gamma) mouse adsorbed (Invitrogen, Cat No. H10500) or anti mouse Fc specific antibody (Jackson Immuno Research Labs inc. Cat No. 515-005-071) were chemically immobilized on a CM-5 sensor surface using standard amine coupling chemistry) and used to capture the mAb from solution. Soluble human IL-3Rα was then injected over captured antibody at various concentrations. Responses were subtracted from those from a reference flow cell in which antibody was not captured, but otherwise treated identically. The reference subtracted responses were then subtracted from the responses from a blank injection.

The final corrected responses were fitted using non-linear regression to a model describing 1:1 kinetics, including a term for mass transport limitation. The Rmax value was fitted locally, to account for slight deviations in the level of antibody captured. Association rate (ka), dissociation rate (kd) and equilibrium dissociation constant ($K_D$) were determined.

Antibodies were captured at 0.3 µg/ml for 180 seconds

Soluble IL-3Rα was injected for 10 minutes, and dissociation was monitored for 30 minutes.

Soluble IL-3Rα was injected at 0, 0.62, 1.25, 2.5, 5, 10, 20 and 40 nM, with 2.5 and 5 nM in duplicate Regeneration was performed after each cycle with a 90 second injection of 100 mM $H_3PO_4$ The assay was conducted at 25° C.

scFv Kinetics:

To analyze scFvs, soluble human IL-3Rα was chemically immobilized on a CM-5 sensor surface using standard amine coupling chemistry, and scFvs were injected at various concentrations. Responses were subtracted from those from a reference flow cell in which IL-3Rα was not immobilized, but otherwise treated identically. The reference subtracted responses were then subtracted from the responses from a blank injection.

The final corrected responses were fitted using non-linear regression to a model describing 1:1 kinetics, including a term for mass transport limitation. The Rmax value was fitted globally, and association rate (ka), dissociation rate (kd) and equilibrium dissociation constant ($K_D$) were determined scFvs were injected for 10 minutes, and dissociation was monitored for 20 minutes.

scFvs were injected at 0, 0.62, 1.25, 2.5, 5, 10, 20 and 40 nM, with 10 nM in duplicate Regeneration was performed after each cycle with a 30 second injection of 100 mM $H_3PO_4$, 1M NaCl and a 15 second injection of 50 mM NaOH.

The assay was conducted at 25° C.

Antibody and scFv affinities are tabulated below in Table 2:

TABLE 2

| Affinity dissociation constants of antibodies and scFvs | |
|---|---|
| Antibody | KD (M) |
| parental murine mAb (7G3) | ~9.2 × 10⁻¹⁰ |
| chimeric form of parental murine mAb) (human $IgG_1$) | ~1.0 × 10⁻⁹ |
| Superhumanized mAb ($IgG_1$) | ~1 × 10⁻⁸ |
| Superhumanized mAb scFv | ~1.4 × 10⁻⁸ |
| CSL362 scFv | ~2.2 × 10⁻⁹ |
| CSL362 ($IgG_1$) | ~7.8 × 10⁻¹⁰ |
| CSL362B | ~4.3 × 10⁻¹⁰ |

Example 3

NK Cell Levels Following Administration of Humanized or Chimeric Antibodies

Naive monkeys (non-human primates; NHPs) were administered a single dose of CSL362B or CSL362X1 via intravenous infusion. In a separate study naïve monkeys were administered repeat doses (weekly ×4) of a chimeric antibody comprising the variable regions of the murine antibody used to produce the humanized antibody (7G3) and a human $IgG_1$ constant region). Peripheral blood was collected at various time points and analysis of NHP NK cells performed by flow cytometry.

As shown in FIG. 1A administration of CSL362X1 resulted in an initial depletion of NK cells, e.g., about 6 hours following administration. At dosages of 0.01 mg/kg and 0.1 mg/kg, this level had exceeded the level observed prior to administration by about 8 days after administration and remained elevated until at least 22 or 29 days after administration. An increase in the number of NK cells was also observed at the 1 mg/kg dosage.

Figure 1B:
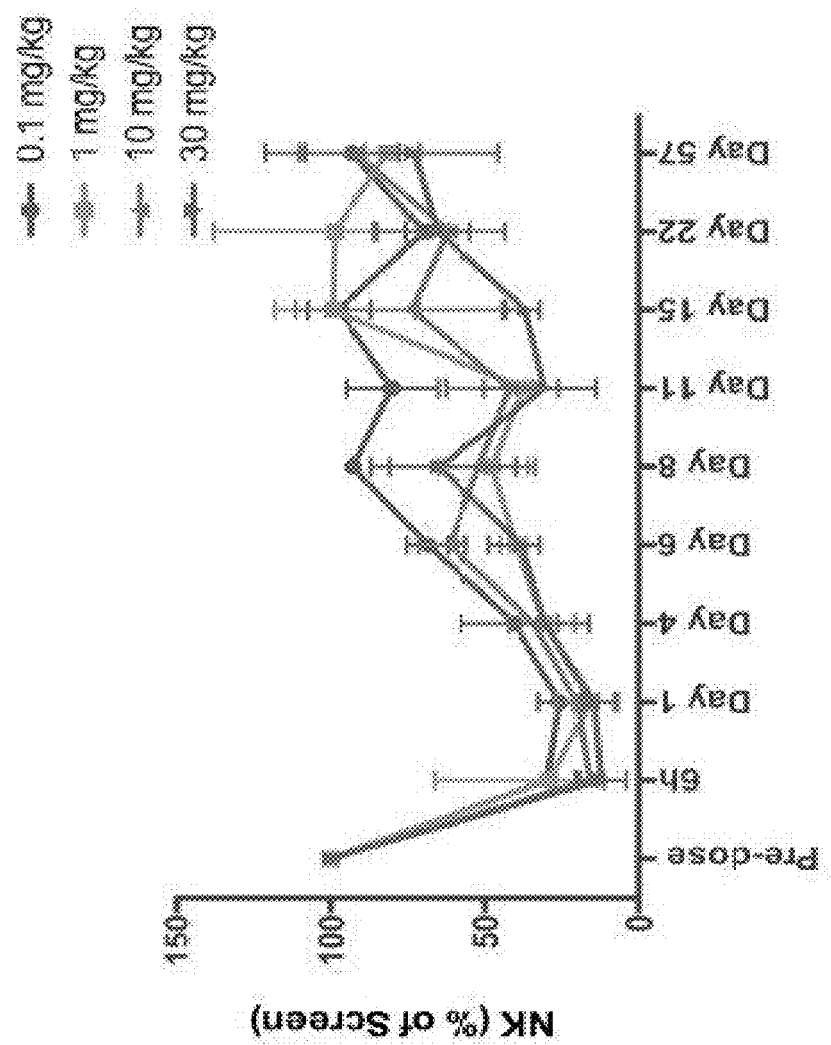
FIG. 1B is a graphical representation showing the number of NK cells in a sample from a non-human primate subject at various time points (as indicated) following administration of antibody CSL362B. The number of cells is represented as a percentage of the number of cells prior to administering the antibody. Dosages of the antibody are indicated.

In contrast to the results described in the previous paragraph, administration of CSL362B resulted in depletion of NK cells, however the NK cell numbers did not subsequently exceed the numbers prior to administration (FIG. 1B).

Figure 1C:
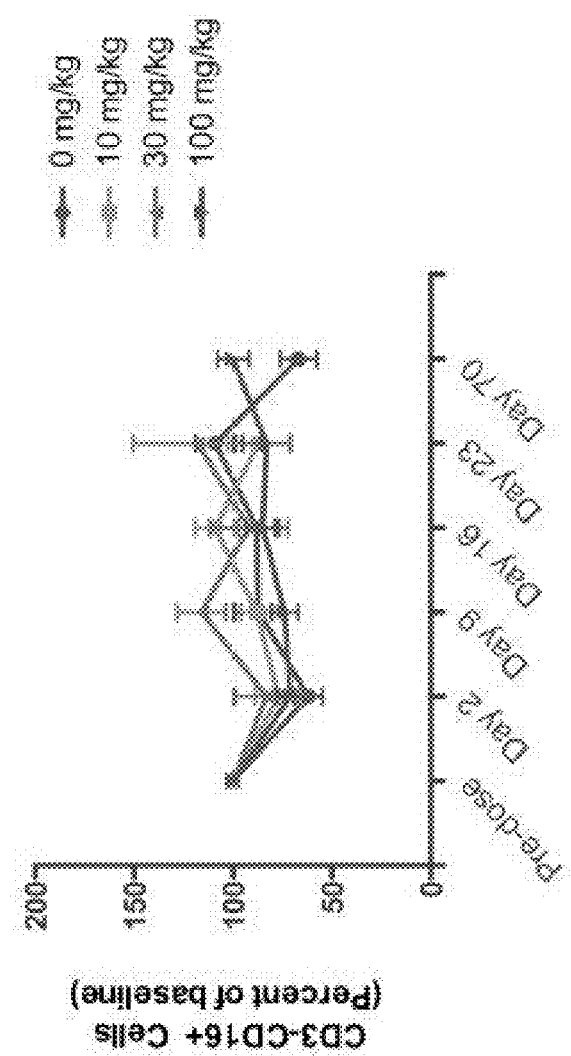
FIG. 1C is a graphical representation showing the number of NK cells in a sample from a non-human primate subject at various time points (as indicated) following administration of a chimeric antibody (designated CSL360) comprising a human IgG1 constant domain and the variable region of antibody 7G3. The number of cells is represented as a percentage of the number of cells prior to administering the antibody. Dosages of the antibody are indicated.

Repeat administration of the chimeric antibody did not substantially change the number of NK cells detected in circulation (FIG. 1C).

Example 4

Enhanced ADCC of Humanized Antibodies in the Presence of NK Cells

Human PBMCs or NK cells were isolated and incubated with TF-1 cells in the presence of various concentrations of CSL362X1. Effector Cells (E; PBMC) and Target cells (T; TF-1 cells) were combined to achieve a ratio of 50:1 (E:T Ratio) or in the case where purified NK cells were used as effectors the ratio was 20:1. Cell lysis was measured using a LDH CytoTox 96 Non-Radioactive Cytotoxicity kit (Promega).

Specific Lysis was determined by the following calculation:

Specific Lysis=[Sample Lysis−Spontaneous Lysis]/ [Maximal Lysis−Spontaneous Lysis]×100%.

Maximal Lysis was evaluated by addition of Extran™ to a final concentration of 0.75% (v/v). Spontaneous Lysis was that which occurred in wells with cells alone (no Ab).

Figure 2A:
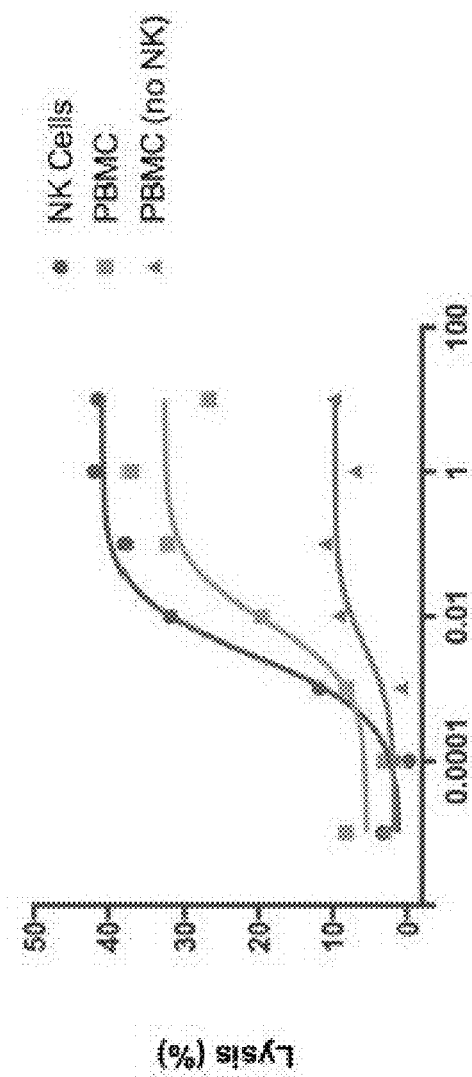
FIG. 2A is a graphical representation showing the percentage of TF-1 cells lysed in the presence of the indicated cell population and antibody CSL362X1 at various concentrations (as indicated on the X axis).

As shown in FIG. 2A, lysis of TF-1 cells occurred in the presence of PBMCs and in the presence of NK cells, however was substantially reduced in PBMCs from which NK cells were removed.

Figure 2B:
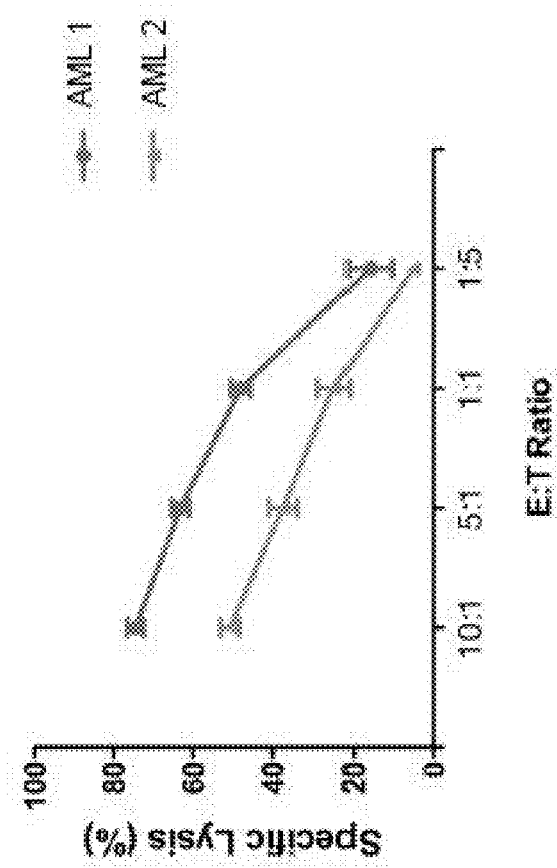
FIG. 2B is a graphical representation showing the percentage of AML cells in the presence of various numbers of NK cells and antibody CSL362X1. The ratio of effector cells (NK cells; E) to target cells (leukemia cells; T) is indicated on the X axis. Results generated suing cells from two patients are depicted.

In a separate experiment, leukemic cells from two different AML patients were used as target cells. In this assay, a single concentration of antibody (10 µg/mL) was used and purified NK cells were added to generate various E:T ratios. FIG. 2B shows that the higher the number of NK cells to target cells (peripheral blood blasts from two different AML patients) (i.e., the E:T ratio), the greater the specific lysis of the target cells by the humanized antibody.

---

The invention claimed is:

1. An isolated or recombinant antibody, which is capable of specifically binding to interleukin (IL)-3Rα chain, wherein the antibody comprises:
   (i) a light chain variable region ($V_L$) comprising CDRs 1, 2 and 3 as set forth in SEQ ID NOs: 2, 3 and 4, respectively;
   (ii) a heavy chain variable region ($V_H$) comprising CDRs 1, 2 and 3 as set forth in SEQ ID NOs: 5, 6 and 7, respectively; and
   (iii) a heavy chain constant region comprising amino acid substitutions S239D and I332E according to the EU numbering system of Kabat.

2. The isolated or recombinant antibody of claim 1, which is a humanized antibody, the antibody comprising:
   (i) a light chain variable region ($V_L$) comprising an amino acid sequence according to SEQ ID NO: 8 and a heavy chain variable region ($V_H$) comprising an amino acid sequence according to SEQ ID NO: 9; and
   (ii) a heavy chain constant region comprising amino acid substitutions S239D and I332E according to the EU numbering system of Kabat.

3. The antibody of claim 1, wherein the heavy chain constant region constant region comprises a sequence set forth between residues 121-450 (inclusive) of SEQ ID NO: 11.

4. The antibody of claim 1, wherein the antibody is a humanized antibody comprising a light chain comprising a sequence set forth in SEQ ID NO: 13 and a heavy chain comprising a sequence set forth in SEQ ID NO: 11.

* * * * *

SEQUENCE LISTING

<160> NUMBER OF SEQ ID NOS: 23

<210> SEQ ID NO 1
<211> LENGTH: 359
<212> TYPE: PRT
<213> ORGANISM: Homo sapiens

<400> SEQUENCE: 1

```
Lys Glu Asp Pro Asn Pro Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
        35                  40                  45

Cys Gln Phe Gly Ala Ile Ser Leu Cys Glu Val Thr Asn Tyr Thr Val
    50                  55                  60

Arg Val Ala Asn Pro Pro Phe Ser Thr Trp Ile Leu Phe Pro Glu Asn
65                  70                  75                  80

Ser Gly Lys Pro Trp Ala Gly Ala Glu Asn Leu Thr Cys Trp Ile His
                85                  90                  95

Asp Val Asp Phe Leu Ser Cys Ser Trp Ala Val Gly Pro Gly Ala Pro
            100                 105                 110

Ala Asp Val Gln Tyr Asp Leu Tyr Leu Asn Val Ala Asn Arg Arg Gln
        115                 120                 125

Gln Tyr Glu Cys Leu His Tyr Lys Thr Asp Ala Gln Gly Thr Arg Ile
    130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                165                 170                 175

Thr Asp Lys Phe Val Val Phe Ser Gln Ile Glu Ile Leu Thr Pro Pro
            180                 185                 190

Asn Met Thr Ala Lys Cys Asn Lys Thr His Ser Phe Met His Trp Lys
        195                 200                 205

Met Arg Ser His Phe Asn Arg Lys Phe Arg Tyr Glu Leu Gln Ile Gln
    210                 215                 220
```

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
            245                 250                 255

Glu Arg Val Tyr Glu Phe Leu Ser Ala Trp Ser Thr Pro Gln Arg Phe
            260                 265                 270

Glu Cys Asp Gln Glu Glu Gly Ala Asn Thr Arg Ala Trp Arg Thr Ser
            275                 280                 285

Leu Leu Ile Ala Leu Gly Thr Leu Leu Ala Leu Val Cys Val Phe Val
            290                 295                 300

Ile Cys Arg Arg Tyr Leu Val Met Gln Arg Leu Phe Pro Arg Ile Pro
305                 310                 315                 320

His Met Lys Asp Pro Ile Gly Asp Ser Phe Gln Asn Asp Lys Leu Val
                325                 330                 335

Val Trp Glu Ala Gly Lys Ala Gly Leu Glu Glu Cys Leu Val Thr Glu
                340                 345                 350

Val Gln Val Val Gln Lys Thr
            355

<210> SEQ ID NO 2
<211> LENGTH: 17
<212> TYPE: PRT
<213> ORGANISM: Artificial Sequence
<220> FEATURE:
<223> OTHER INFORMATION: amino acid sequence of LCDR1 of humanized anti-
      IL-3Ralpha chain antibody CSL362 and modified forms thereof

<400> SEQUENCE: 2

Glu Ser Ser Gln Ser Leu Leu Asn Ser Gly Asn Gln Lys Asn Tyr Leu
1               5                   10                  15

Thr

<210> SEQ ID NO 3
<211> LENGTH: 7
<212> TYPE: PRT
<213> ORGANISM: Artificial Sequence
<220> FEATURE:
<223> OTHER INFORMATION: amino acid sequence of LCDR2 of humanized anti-
      IL-3Ralpha chain antibody CSL362 and modified forms thereof

<400> SEQUENCE: 3

Trp Ala Ser Thr Arg Glu Ser
1               5

<210> SEQ ID NO 4
<211> LENGTH: 9
<212> TYPE: PRT
<213> ORGANISM: Artificial Sequence
<220> FEATURE:
<223> OTHER INFORMATION: amino acid sequence of LCDR3 of humanized anti-
      IL-3Ralpha chain antibody CSL362 and modified forms thereof

<400> SEQUENCE: 4

Gln Asn Asp Tyr Ser Tyr Pro Tyr Thr
1               5

<210> SEQ ID NO 5
<211> LENGTH: 5
<212> TYPE: PRT
<213> ORGANISM: Artificial Sequence
<220> FEATURE:
<223> OTHER INFORMATION: amino acid sequence of HCDR1 of humanized anti-
      IL-3Ralpha chain antibody CSL362 and modified forms thereof

```
<400> SEQUENCE: 5

Asp Tyr Tyr Met Lys
1               5

<210> SEQ ID NO 6
<211> LENGTH: 17
<212> TYPE: PRT
<213> ORGANISM: Artificial Sequence
<220> FEATURE:
<223> OTHER INFORMATION: amino acid sequence of HCDR2 of humanized anti-
      IL-3Ralpha chain antibody CSL362 and modified forms thereof

<400> SEQUENCE: 6

Asp Ile Ile Pro Ser Asn Gly Ala Thr Phe Tyr Asn Gln Lys Phe Lys
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: mino acid sequence of HCDR3 of a humanized
      anti- IL-3R alpha chain antibody

<400> SEQUENCE: 7

Ser His Leu Leu Arg Ala Ser Trp Phe Ala Tyr
1               5                   10

<210> SEQ ID NO 8
<211> LENGTH: 114
<212> TYPE: PRT
<213> ORGANISM: Artificial Sequence
<220> FEATURE:
<223> OTHER INFORMATION: amino acid sequence of light chain variable
      region of humanized anti- IL-3Ralpha chain antibody CSL362 and
      modified forms thereof

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg

<210> SEQ ID NO 9
<211> LENGTH: 120
<212> TYPE: PRT
<213> ORGANISM: Artificial Sequence
<220> FEATURE:
<223> OTHER INFORMATION: amino acid sequence of heavy chain variable
      region of humanized anti- IL-3Ralpha chain antibody CSL362 and
      modified forms thereof
```

```
<400> SEQUENCE: 9

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser
        115                 120

<210> SEQ ID NO 10
<211> LENGTH: 450
<212> TYPE: PRT
<213> ORGANISM: Artificial Sequence
<220> FEATURE:
<223> OTHER INFORMATION: amino acid sequence of heavy chain of
      humanized anti- IL-3Ralpha chain antibody CSL362 and CSL362B

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 11
<211> LENGTH: 450
<212> TYPE: PRT
<213> ORGANISM: Artificial Sequence
<220> FEATURE:
<223> OTHER INFORMATION: amino acid sequence of heavy chain of humanized
      anti- IL-3Ralpha chain antibody CSL362X1

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
            85                  90                  95

Ala Arg Ser His Leu Leu Arg Ala Ser Trp Phe Ala Tyr Trp Gly Gln
        100                 105                 110

Gly Thr Met Val Thr Val Ser Ser Ala Ser Thr Lys Gly Pro Ser Val
    115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Thr Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 12
<211> LENGTH: 450
<212> TYPE: PRT
<213> ORGANISM: Artificial Sequence
<220> FEATURE:
<223> OTHER INFORMATION: amino acid sequence of heavy chain of humanized
      anti- IL-3Ralpha chain antibody CSL362X2

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30
```

```
Tyr Met Lys Trp Ala Arg Gln Met Pro Gly Lys Gly Leu Glu Trp Met
     35                  40                  45
Gly Asp Ile Ile Pro Ser Asn Gly Ala Thr Phe Tyr Asn Gln Lys Phe
 50                  55                  60
Lys Gly Gln Val Thr Ile Ser Ala Asp Lys Ser Ile Ser Thr Thr Tyr
 65                  70                  75                  80
Leu Gln Trp Ser Ser Leu Lys Ala Ser Asp Thr Ala Met Tyr Tyr Cys
                 85                  90                  95
Ala Arg Ser His Leu Leu Arg Ala Ser Trp Phe Ala Tyr Trp Gly Gln
                100                 105                 110
Gly Thr Met Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Asp Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Phe Arg
290                 295                 300
Val Val Ser Val Leu Thr Val His Gln Asp Trp Leu Asn Gly Lys
305                 310                 315                 320
Glu Tyr Lys Cys Lys Val Ser Asn Lys Ala Leu Pro Leu Pro Glu Glu
                325                 330                 335
Lys Thr Ile Ser Lys Thr Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Met
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

<210> SEQ ID NO 13
<211> LENGTH: 220
<212> TYPE: PRT
<213> ORGANISM: Artificial Sequence
<220> FEATURE:
<223> OTHER INFORMATION: amino acid sequence of light chain of humanized
      anti- IL-3Ralpha chain antibody CSL362 and modified forms thereof

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 14
<211> LENGTH: 51
<212> TYPE: DNA
<213> ORGANISM: Artificial Sequence
<220> FEATURE:
<223> OTHER INFORMATION: nucleotide sequence encoding a LCDR1 of
      humanized anti- IL-3Ralpha chain antibody CSL362 and modified
      forms thereof

<400> SEQUENCE: 14
gagagcagcc agagcctgct gaacagcggc aaccagaaga actacctgac c        51

<210> SEQ ID NO 15
<211> LENGTH: 21
<212> TYPE: DNA
<213> ORGANISM: Artificial Sequence
<220> FEATURE:
<223> OTHER INFORMATION: nucleotide sequence encoding a LCDR2 of
      humanized anti- IL-3Ralpha chain antibody CSL362 and modified
      forms thereof

<400> SEQUENCE: 15

```
tgggccagca cccgggagag c                                              21
```

<210> SEQ ID NO 16
<211> LENGTH: 27
<212> TYPE: DNA
<213> ORGANISM: Artificial Sequence
<220> FEATURE:
<223> OTHER INFORMATION: nucleotide sequence encoding a LCDR3 of
      humanized anti- IL-3Ralpha chain antibody CSL362 and modified
      forms thereof

<400> SEQUENCE: 16

```
cagaacgact acagctaccc ctacacc                                        27
```

<210> SEQ ID NO 17
<211> LENGTH: 15
<212> TYPE: DNA
<213> ORGANISM: Artificial Sequence
<220> FEATURE:
<223> OTHER INFORMATION: nucleotide sequence encoding a HCDR1 of
      humanized anti- IL-3Ralpha chain antibody CSL362 and modified
      forms thereof

<400> SEQUENCE: 17

```
gactactaca tgaag                                                     15
```

<210> SEQ ID NO 18
<211> LENGTH: 51
<212> TYPE: DNA
<213> ORGANISM: Artificial Sequence
<220> FEATURE:
<223> OTHER INFORMATION: nucleotide sequence encoding a HCDR2 of
      humanized anti- IL-3Ralpha chain antibody CSL362 and modified
      forms thereof

<400> SEQUENCE: 18

```
gacatcatcc ccagcaacgg cgccaccttc tacaaccaga agttcaaggg c             51
```

<210> SEQ ID NO 19
<211> LENGTH: 33
<212> TYPE: DNA
<213> ORGANISM: Artificial Sequence
<220> FEATURE:
<223> OTHER INFORMATION: nucleotide sequence encoding a HCDR3 of
      humanized anti- IL-3Ralpha chain antibody CSL362 and modified
      forms thereof

<400> SEQUENCE: 19

```
tcccacctgc tgagggccag ctggttcgcc tac                                 33
```

<210> SEQ ID NO 20
<211> LENGTH: 342
<212> TYPE: DNA
<213> ORGANISM: Artificial Sequence
<220> FEATURE:
<223> OTHER INFORMATION: nucleotide sequence encoding a light chain
      variable region of humanized anti- IL-3Ralpha chain antibody
      CSL362 and modified forms thereof

<400> SEQUENCE: 20

```
gacatcgtga tgacccagag ccccgacagc ctggccgtga gcctgggcga gagggccacc    60
atcaactgcg agagcagcca gagcctgctg aacagcggca accagaagaa ctacctgacc   120
tggtatcagc agaagcccgg ccagccccccc aagccactga tctactgggc cagcacccgg   180
gagagcggcg tgcccgacag gttcagcggc agcggctccg gcaccgactt caccctgacc   240
atcagcagcc tgcaggccga ggacgtggcc gtgtactact gccagaacga ctacagctac   300
```

```
ccctacacct tcggccaggg caccaagctg gaaatcaaga gg           342
```

<210> SEQ ID NO 21
<211> LENGTH: 360
<212> TYPE: DNA
<213> ORGANISM: Artificial Sequence
<220> FEATURE:
<223> OTHER INFORMATION: nucleotide sequence encoding a heavy chain
      variable region of humanized anti- IL-3Ralpha chain antibody
      CSL362 and modified forms thereof

<400> SEQUENCE: 21

```
gaggtgcagc tggtgcagag cggagccgag gtgaagaagc ccggcgagag cctgaagatc    60
agctgcaagg gcagcggcta cagcttcacc gactactaca tgaagtgggc ccggcagatg   120
cccggcaagg gcctggaatg gatgggcgac atcatcccca gcaacggcgc caccttctac   180
aaccagaagt tcaagggcca ggtcaccatc agcgccgaca gagcatcag caccacctac   240
ctgcagtgga gcagcctgaa ggccagcgac accgccatgt actactgcgc caggtcccac   300
ctgctgaggg ccagctggtt cgcctactgg ggccagggca atggtgac cgtgagcagc   360
```

<210> SEQ ID NO 22
<211> LENGTH: 1353
<212> TYPE: DNA
<213> ORGANISM: Artificial Sequence
<220> FEATURE:
<223> OTHER INFORMATION: nucleotide sequence encoding a heavy chain of
      humanized anti- IL-3Ralpha chain antibody CSL362 and CSL362B

<400> SEQUENCE: 22

```
gaggtgcagc tggtgcagag cggagccgag gtgaagaagc ccggcgagag cctgaagatc    60
agctgcaagg gcagcggcta cagcttcacc gactactaca tgaagtgggc ccggcagatg   120
cccggcaagg gcctggaatg gatgggcgac atcatcccca gcaacggcgc caccttctac   180
aaccagaagt tcaagggcca ggtcaccatc agcgccgaca gagcatcag caccacctac   240
ctgcagtgga gcagcctgaa ggccagcgac accgccatgt actactgcgc caggtcccac   300
ctgctgaggg ccagctggtt cgcctactgg ggccagggca atggtgac cgtgagcagc   360
gctagcacca agggcccag cgtgttcccc ctggccccca gcagcaagag caccagcggc   420
ggcacagcag ccctgggatg cctggtgaag gactacttcc ccgagcccgt gaccgtgtcc   480
tggaacagcg gagccctgac ctccggcgtg cacaccttcc ccgccgtgct gcagagcagc   540
ggcctgtatt ctctgagcag cgtcgtgaca gtgcccagca gcagcctggg cacccagacc   600
tacatctgca acgtgaacca caagcccagc aacaccaagg tggacaagaa ggtggagccc   660
aagagctgcg acaagaccca cacctgtcct ccatgcccag ccccagagct gctgggcgga   720
ccctccgtgt tcctgttccc ccccaagccc aaggacaccc tgatgatcag caggacccc   780
gaggtgacct gcgtggtggt ggacgtgagc cacgaggacc cagaggtgaa gttcaactgg   840
tacgtggacg gcgtggaggt gcacaacgcc aagaccaagc cagagagga acagtacaac   900
agcacctaca gggtggtgtc cgtgctgacc gtgctgcacc aggactggct gaacggcaag   960
gagtacaagt gcaaagtctc caacaaggcc ctgccagccc ccatcgagaa aaccatcagc  1020
aaggccaagg gccagccacg ggagcccag gtgtacaccc tgccccctc ccgggacgag  1080
ctgaccaaga accaggtgtc cctgacctgt ctggtgaagg gcttctaccc cagcgacatt  1140
gccgtggagt gggagagcaa cggccagccc gagaacaact acaagaccac ccccccagtg  1200
ctggacagcg acggcagctt cttcctgtac agcaagctga ccgtggacaa gagcaggtgg  1260
cagcagggca acgtgttcag ctgcagcgtg atgcacgagg ccctgcacaa ccactacacc  1320
```

```
cagaagagcc tgagcctgtc ccccggcaag tga                                 1353

<210> SEQ ID NO 23
<211> LENGTH: 663
<212> TYPE: DNA
<213> ORGANISM: Artificial Sequence
<220> FEATURE:
<223> OTHER INFORMATION: nucleotide sequence encoding a light chain of
      humanized anti- IL-3Ralpha chain antibody CSL362 and modified
      forms thereof

<400> SEQUENCE: 23
gacatcgtga tgacccagag ccccgacagc ctggccgtga gcctgggcga gagggccacc     60
atcaactgcg agagcagcca gagcctgctg aacagcggca accagaagaa ctacctgacc    120
tggtatcagc agaagcccgg ccagcccccc aagccactga tctactgggc cagcacccgg    180
gagagcggcg tgcccgacag gttcagcggc agcggctccg gcaccgactt caccctgacc    240
atcagcagcc tgcaggccga ggacgtggcc gtgtactact gccagaacga ctacagctac    300
ccctacacct tcggccaggg caccaagctg gaaatcaaga ggaccgtggc tgccccatct    360
gtcttcatct tccccccag cgacgagcag ctgaagagcg gcaccgccag cgtggtgtgc    420
ctgctgaata acttctaccc ccgggaggcc aaggtgcagt ggaaggtgga caacgccctg    480
cagagcggca acagccagga aagcgtcacc gagcaggaca gcaaggactc cacctacagc    540
ctgagcagca ccctgaccct gagcaaggcc gactacgaga agcacaaggt gtacgcctgc    600
gaggtgaccc accagggcct gtccagcccc gtgaccaaga gcttcaacag gggcgagtgc    660
tga                                                                 663
```